US009930703B2

(12) United States Patent
Lee et al.

(10) Patent No.: US 9,930,703 B2
(45) Date of Patent: Mar. 27, 2018

(54) ELECTRONIC DEVICE, OPERATING METHOD THEREOF, AND RECORDING MEDIUM

(71) Applicant: Samsung Electronics Co., Ltd., Suwon-si, Gyeonggi-do (KR)

(72) Inventors: Jae-Wook Lee, Suwon-si (KR); Ju-Yeon Seo, Suwon-si (KR); Seong-Ki Ryu, Suwon-si (KR); Jae-Seok Joo, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/146,566

(22) Filed: May 4, 2016

(65) Prior Publication Data

US 2016/0330770 A1 Nov. 10, 2016

(30) Foreign Application Priority Data

May 7, 2015 (KR) ........................ 10-2015-0063913

(51) Int. Cl.
*H04M 11/04* (2006.01)
*H04W 76/00* (2018.01)
*G06F 19/00* (2018.01)
*H04W 4/02* (2018.01)

(52) U.S. Cl.
CPC ...... *H04W 76/007* (2013.01); *G06F 19/3431* (2013.01); *H04W 4/025* (2013.01)

(58) Field of Classification Search
CPC .. H04W 76/007; H04W 4/025; G06F 19/3431
See application file for complete search history.

(56) References Cited

U.S. PATENT DOCUMENTS

| 2009/0088607 | A1 | 4/2009 | Muraca |
| 2009/0089089 | A1 | 4/2009 | Jang et al. |
| 2013/0109417 | A1 | 5/2013 | Nawy et al. |
| 2013/0166322 | A1* | 6/2013 | Woods .................. G06F 19/322 705/3 |
| 2014/0315513 | A1* | 10/2014 | Long ...................... H04W 4/22 455/404.2 |
| 2015/0099458 | A1* | 4/2015 | Weisner ................ H04W 84/22 455/15 |

(Continued)

FOREIGN PATENT DOCUMENTS

| KR | 10-2001-0053574 A | 6/2001 |
| KR | 10-2003-0058402 A | 7/2003 |

(Continued)

*Primary Examiner* — Wayne Cai

(74) *Attorney, Agent, or Firm* — Jefferson IP Law, LLP

(57) ABSTRACT

An electronic device, an operating method thereof, and a recording medium are provided. The electronic device includes a housing, a location sensor that is disposed within the housing and obtains location information about the electronic device, a biometric sensor that is disposed within the housing and obtains health information about a user of the electronic device, and a processor which is disposed within the housing, and is connected with the location sensor and the biometric sensor, wherein when a change to an emergency mode is detected, the processor controls to transmit the location information and the health information to a predesignated first external electronic device in response to the emergency mode.

18 Claims, 21 Drawing Sheets

(56) References Cited

U.S. PATENT DOCUMENTS

2015/0213194 A1* 7/2015 Wolf ............... G06F 19/322
                                                    705/3
2015/0223705 A1* 8/2015 Sadhu ............... G01S 19/17
                                                    600/301

FOREIGN PATENT DOCUMENTS

| KR | 10-2007-0057586 A | 6/2007 |
| KR | 10-2007-0062215 A | 6/2007 |
| KR | 10-0821628 B1 | 4/2008 |
| KR | 10-0855616 B1 | 9/2008 |
| KR | 10-2009-0032339 A | 4/2009 |
| KR | 10-2010-0045923 A | 5/2010 |
| KR | 10-2010-0086596 A | 8/2010 |

* cited by examiner

Request Element Type

| Description | REQ_TYPE (binary) |
|---|---|
| Reserved | '0000' |
| Request MS Information | '0010' |
| Request Autonomous Measurement Weighting Factors | '0011' |
| Request Pseudorange Measurement | '0100' |
| Request Pilot Phase Measurement | '0101' |
| Request Location Response | '0001' |
| Request Time Offset Measurement | '0110' |
| Request Cancellation | '0111' |
| All other REQ_TYPE values are reserved. | |

<BS to MS request command>

Request type define

| Description | Req_type (binary) |
|---|---|
| Request healthcare capability | '1000' |
| Request healthcare information | '1001' |
| Request sensor capability | '1010' |
| Request sensor information | '1101' |
| ... | ... |

FIG.4A

| MS request | | BS request | |
|---|---|---|---|
| Description | REQ_TYPE (binary) | Description | REQ_TYPE (binary) |
| Reserved | '0000' | Reserved | '0000' |
| Request BS capability | '0000' | Request MS information | '0001' |
| ......... | .... | Request health information | '0010' |
| ......... | .... | ......... | .... |
| ......... | .... | ......... | .... |

| VALUE(hex) | Meaning | Classification | Repeatability |
|---|---|---|---|
| 00 | Concatenated short messages, 8-bit reference number | SMS Control | No |
| 01 | Special SMS Message Indication | SMS Control | Yes |
| 02 | Reserved | N/A | N/A |
| 03 | Value not used to avoid misinterpretation as <LF> character | N/A | N/A |
| 04 | Application port addressing scheme, 8bit address | SMS Control | No |
| 05 | Application port addressing scheme, 16bit address | SMS Control | No |

FIG.11B

Port: 2948/TCP

| 2948/TCP-Known port assignments (2records found) | | |
|---|---|---|
| Service | Details | Source |
| wap-push | WAP PUSH | IANA |
|  | WAP-push Multimedia Messaging Service (MMS) (Official) | WIKI |

Port: 2948/UDP

| 2948/UDP-Known port assignments (2records found) | | |
|---|---|---|
| Service | Details | Source |
| wap-push | WAP PUSH | IANA |
|  | WAP-push Multimedia Messaging Service (MMS) (Official) | WIKI |

FIG.11C

ELECTRONIC DEVICE, OPERATING METHOD THEREOF, AND RECORDING MEDIUM

CROSS-REFERENCE TO RELATED APPLICATION

This application claims the benefit under 35 U.S.C. § 119(a) of a Korean patent application filed on May 7, 2015, in the Korean Intellectual Property Office and assigned serial number 10-2015-0063913, the entire disclosure of which is hereby incorporated by reference.

TECHNICAL FIELD

The present disclosure relates to an electronic device, an operating method thereof, and a recording medium.

BACKGROUND

Recently, as electronic devices, such as smart phones, have rapidly propagated, the era of one-man one-device has come. This means that the electronic device is one part of a user's daily life, and users also recognize that it is difficult to lead their daily life without the electronic device. In actuality, the user of the electronic device possesses the electronic device most of the time during his/her daily life, and the average time of the electronic device is used has gradually increased.

As described above, the electronic device becomes a part of the daily life of the user, so that the electronic device includes various functions, (for example, a function of providing the current location information of the user to a rescuer at a physical emergency situation of the user), which are capable of providing actual helps in the daily life of the user.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an electronic device, an operating method thereof, and a recording medium.

The user (in the present disclosure, the user may also be referred to as a "help requester" as necessary) may not be able to continue a call for requesting help due to a physical problem (for example, a heart attack or diabetes) of the help requester after a call connection (for example, a 119 call connection) for requesting help from the rescuer. For example, after the call connection for requesting the help, a situation may occur in which the user has difficulty in continuing the call for requesting help due to the help requester suffering from a heart attack. In this case, according to the related art related to the rescue of the help requester, the rescuer cannot confirm a current physical problem, such as a heart attack, of the help requester, so that there is a case where it is difficult to achieve the purpose of the call for requesting the help, such as the treating the call for requesting help as a nuisance phone call.

Further, according to the related art related to the emergency situation, there may be a case where during a process of rescuing the help requester after receiving the help request, an appropriate rescue activity may not be performed due to the physical problem (for example, diabetes) of the help requester, which the help requester fails to explain to the rescuer during the call for requesting the help. For example, the rescuer recognizes the current state of the help requester through the call for requesting the help and brought an emergency medication "injections A" for rescuing the help requester, but the "injections A" may be a medication of which the injection to a diabetic patient is prohibited. As described above, according to the related art related to the help of the help requester, a case may occur where the rescuer fails to accurately understand the physical problem of the help requester, so that the rescuer cannot appropriately take actions during a process of helping the help requester.

The present disclosure discloses an electronic device, which enables a rescuer to accurately determine the current state of a help requester (for example, a current symptom of the help requester and/or the kind of diseases of the help requester) by transmitting health information (that is, a physical state) about the help requester to the rescuer, as well as information on the current location of the rescue requester, thereby rapidly performing a rescue activity when an emergency situation is generated.

The present disclosure discloses a method of operating an electronic device, which enables a rescuer to accurately determine the current state of a help requester (for example, a current symptom of the help requester and/or the kind of diseases of the help requester) and to rapidly perform a rescue activity by transmitting health information (that is, a physical state) about the help requester to the rescuer, as well as information on the current location of the rescue requester when an emergency situation is generated.

The technical objectives disclosed in the present disclosure are not limited to the aforementioned technical objectives, and unmentioned or other technical objectives will be clearly appreciated by those skilled in the art from the following description.

In accordance with an aspect of the present disclosure, an electronic device is provided. The electronic device includes a housing, a location sensor that is disposed within the housing and obtains location information about the electronic device, a biometric sensor that is disposed within the housing and obtains health information about a user of the electronic device, and a processor which is disposed within the housing, and is connected with the location sensor and the biometric sensor, wherein when a change to an emergency mode is detected, the processor controls to transmit the location information and the health information to a predesignated first external electronic device in response to the emergency mode.

In accordance with another aspect of the present disclosure, an electronic device is provided. The electronic device includes a housing, a location sensor that is disposed within the housing and obtains location information about the electronic device, a biometric sensor that is disposed within the housing and obtains health information about a user of the electronic device, and a processor which is disposed within the housing, and is connected with the location sensor and the biometric sensor, wherein the processor changes an operation mode of the electronic device to an emergency mode based on the obtained health information, controls to transmit the location information of the electronic device and the obtained health information to a predesignated first external electronic device, and controls to transmit the location information and at least one piece of health information corresponding to a response to the external electronic device according to the response transmitted from the first external electronic device in response to the transmission of the health information.

In accordance with another aspect of the present disclosure, a method of operating an electronic device is provided. The method includes when a mode change event is detected, changing an operation mode of the electronic device to an emergency mode according to the detected mode change event, obtaining location information about the electronic device and health information about a user in the emergency mode, and transmitting the obtained location information and health information to a predesignated first external electronic device in response to the emergency mode.

In accordance with another aspect of the present disclosure, a method of operating an electronic device is provided. The method includes obtaining location information about the electronic device and health information about a user, when the obtained health information passes a predetermined threshold value, transmitting the obtained location information and health information to a predesignated external electronic device, and transmitting the location information and at least one piece of health information corresponding to a response to the external electronic device according to the response transmitted from the external electronic device in response to the transmission of the health information.

In accordance with another aspect of the present disclosure, a computer readable recoding medium is provided. The computer readable recoding medium stores instructions set to perform one or more operations by a processor. The one or more operations include obtaining location information about the electronic device and health information about a user, when the obtained health information passes a predetermined threshold value, transmitting the obtained location information and health information to a predesignated external electronic device, and transmitting the location information and at least one health information corresponding to a response to the external electronic device according to the response transmitted from the external electronic device in response to the transmission of the health information.

In accordance with yet another aspect of the present disclosure, a computer readable recoding medium is provided. The computer readable recoding medium stores instructions set to perform one or more operations by a processor. The one or more operations include obtaining location information about the electronic device and health information about a user, when the obtained health information passes a predetermined threshold value, transmitting the obtained location information and health information to a predesignated external electronic device, and transmitting the location information and at least one health information corresponding to a response to the external electronic device according to the response transmitted from the external electronic device in response to the transmission of the health information.

According to the present disclosure, it is possible to enable a rescuer to accurately determine the current state of a help requester (for example, a current symptom of the help requester and/or the kind of diseases of the help requester) by transmitting health information (that is, a physical state) about the help requester to the rescuer, as well as information on the current location of the rescue requester, thereby rapidly performing a rescue activity when an emergency situation is generated.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 4A is a diagram for describing an instruction stored in a reserved field according to various embodiments of the present disclosure applied in a synchronous IS-801 protocol;

FIG. 11B is a diagram for an information element identifier (IEI) field among the fields illustrated in FIG. 11A according to various embodiments of the present disclosure;

FIG. 11C is a diagram for a Wireless Application Protocol (WAP) Push port 2948 designated as a multimedia message service (MMS) notification port in an OMA device management (DM) according to various embodiments of the present disclosure;

Throughout the drawings, like reference numerals will be understood to refer to like parts, components, and structures.

DETAILED DESCRIPTION

Figure 1:
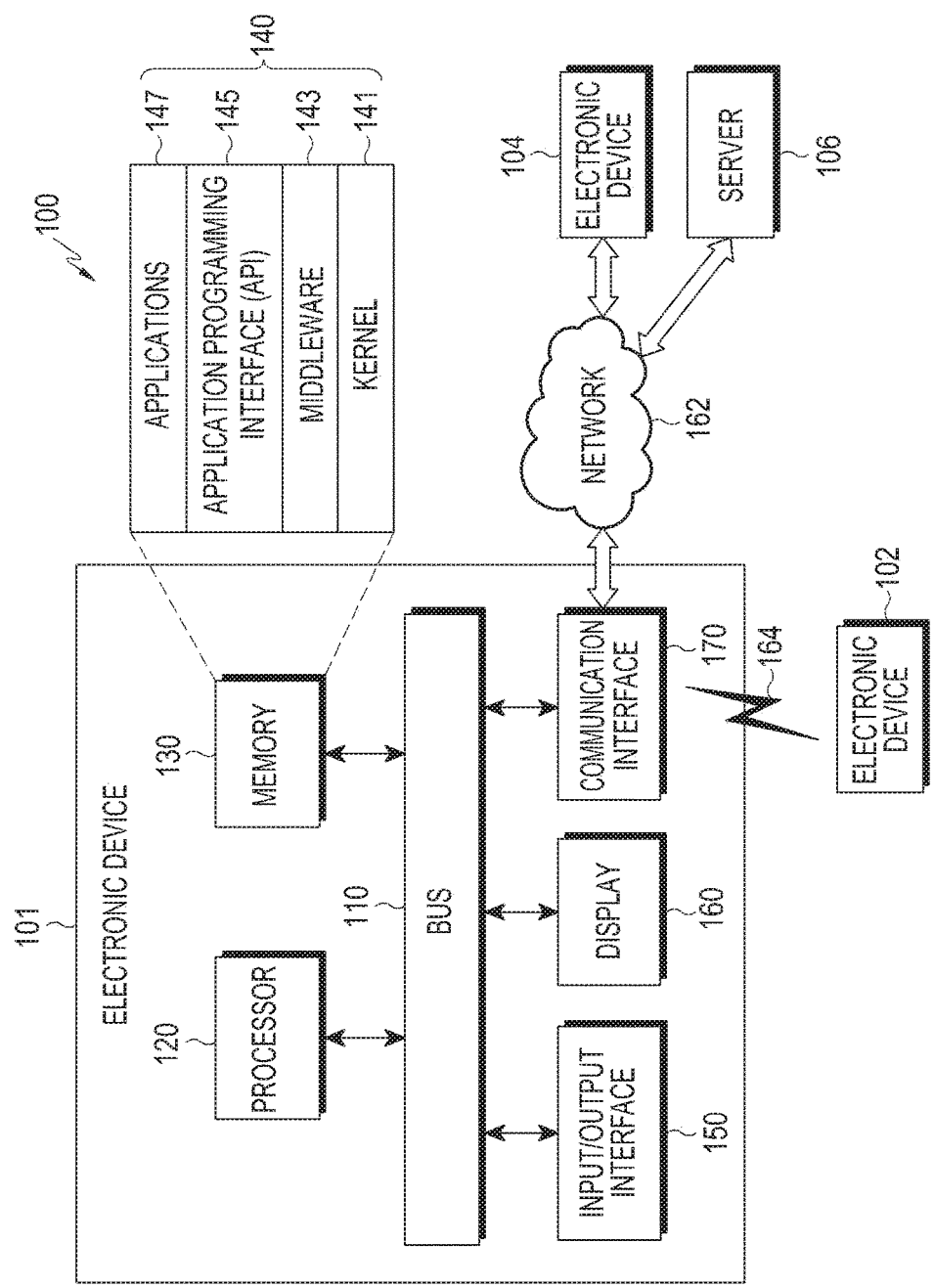
FIG. 1 is a diagram illustrating an example of an electronic device within a network environment according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

As used herein, the expression "have", "may have", "include", or "may include" refers to the existence of a corresponding feature (e.g., numeral, function, operation, or constituent element such as component), and does not exclude one or more additional features.

In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B.

The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in the present disclosure may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. embedded processor) only for performing the corresponding operations or a generic-purpose processor (e.g., central processing unit (CPU) or application processor (AP)) that can perform the corresponding operations by executing one or more software programs stored in a memory device.

The terms used herein are merely for the purpose of describing particular embodiments and are not intended to limit the scope of other embodiments of the present disclosure. A singular expression may include a plural expression unless they are definitely different in a context. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

An electronic device according to various embodiments of the present disclosure may include at least one of, for example, a smart phone, a tablet personal computer (PC), a mobile phone, a video phone, an electronic book reader (e-book reader), a desktop PC, a laptop PC, a netbook computer, a workstation, a server, a personal digital assistant (PDA), a portable multimedia player (PMP), a Moving Picture Experts Group (MPEG-1 of MPEG-2) audio layer-III (MP3) player, a mobile medical device, a camera, and a wearable device. According to various embodiments of the present disclosure, the wearable device may include at least one of an accessory type (e.g., a watch, a ring, a bracelet, an anklet, a necklace, a glasses, a contact lens, or a head-mounted device (HMD)), a fabric or clothing integrated type (e.g., an electronic clothing), a body-mounted type (e.g., a skin pad, or tattoo), and a bio-implantable type (e.g., an implantable circuit).

According to some embodiments of the present disclosure, the electronic device may be a home appliance. The home appliance may include at least one of, for example, a television (TV), a digital versatile disc (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

According to another embodiment of the present disclosure, the electronic device may include at least one of various medical devices (e.g., various portable medical measuring devices (a blood glucose monitoring device, a heart rate monitoring device, a blood pressure measuring device, a body temperature measuring device, etc.), a magnetic resonance angiography (MRA), a magnetic resonance imaging (MRI), a computed tomography (CT) machine, and an ultrasonic machine), a navigation device, a global positioning system (GPS) receiver, an event data recorder (EDR), a flight DR (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.).

According to some embodiments of the present disclosure, the electronic device may include at least one of a part of furniture or a building/structure, an electronic board, an electronic signature receiving device, a projector, and various kinds of measuring instruments (e.g., a water meter, an electric meter, a gas meter, and a radio wave meter). In various embodiments of the present disclosure, the electronic device may be a combination of one or more of the aforementioned various devices. The electronic device according to some embodiments of the present disclosure may be a flexible device. Further, the electronic device according to an embodiment of the present disclosure is not limited to the aforementioned devices, and may include a new electronic device according to the development of technology.

Hereinafter, an electronic device according to various embodiments will be described with reference to the accompanying drawings. As used herein, the term "user" may indicate a person who uses an electronic device or a device (e.g., an artificial intelligence electronic device) that uses an electronic device.

FIG. 1 is a diagram illustrating an example of an electronic device within a network environment according to various embodiments of the present disclosure.

Referring to FIG. 1, an electronic device 101 within a network environment 100, according to various embodiments of the present disclosure, will be described with reference to FIG. 1. The electronic device 101 may include a bus 110, a processor 120, a memory 130, an input/output interface 150, a display 160, and a communication interface 170. In some embodiments of the present disclosure, the electronic device 101 may omit at least one of the above elements or may further include other elements.

The bus 110 may include, for example, a circuit which interconnects the elements 110 to 170 and delivers communication (for example, a control message and/or data) between the elements 110 to 180.

The processor 120 may include one or more of a CPU, an AP, and a communication processor (CP). For example, the processor 120 may carry out operations or data processing relating to the control and/or communication of at least one other element of the electronic device 101.

The memory 130 may include a volatile memory and/or a non-volatile memory. The memory 130 may store, for example, instructions or data related to at least one other element of the electronic device 101. According to an embodiment of the present disclosure, the memory 130 may store software and/or a program 140. The program 140 may include, for example, a kernel 141, middleware 143, an application programming interface (API) 145, and/or application programs (or "applications") 147. At least some of the kernel 141, the middleware 143, and the API 145 may be referred to as an operating system (OS).

For example, the kernel 141 may control or manage system resources (for example, the bus 110, the processor 120, and the memory 130) which are used to execute an operation or a function implemented in the other programs (for example, the middleware 143, the API 145, and the application programs 147). Furthermore, the kernel 141 may provide an interface through which the middleware 143, the API 145, or the application programs 147 may access the individual elements of the electronic device 101 to control or manage the system resources.

The middleware 143 may function as, for example, an intermediary for allowing the API 145 or the application programs 147 to communicate with the kernel 141 to exchange data.

The middleware 143 may process one or more task requests, which are received from the application programs 147, according to priorities thereof. For example, the middleware 143 may assign priorities for using the system resources (for example, the bus 110, the processor 120, and the memory 130) of the electronic device 101, to at least one of the application programs 147. For example, the middleware 143 may perform scheduling or loading balancing on the one or more task requests by processing the one or more task requests according to the priorities assigned thereto.

The API 145 is an interface through which the applications 147 control functions provided from the kernel 141 or the middleware 143, and may include, for example, at least one interface or function (e.g., instruction) for file control, window control, image processing, or text control.

The input/output interface 150, for example, may function as an interface that may transfer a command or data input from a user or another external device to the other element(s) of the electronic device 101. Furthermore, the input/output interface 150 may output the commands or data received from the other element(s) of the electronic device 101 to the user or to another external device.

Examples of the display 160 may include a liquid crystal display (LCD), a light-emitting diode (LED) display, an organic LED (OLED) display, a microelectromechanical systems (MEMS) display, and an electronic paper display. The display 160 may display, for example, various types of contents (for example, text, images, videos, icons, or symbols) for the user. The display 160 may include a touch screen and receive, for example, a touch, gesture, proximity, or hovering input using an electronic pen or the user's body part.

The communication interface 170 may set communication between, for example, the electronic device 101 and an external device (for example, a first external electronic device 102, a second external electronic device 104, or a server 106). For example, the communication interface 170 may be connected to a network 162 through wireless or wired communication to communicate with the external device (for example, the second external electronic device 104 or the server 106).

The wireless communication may use at least one of, for example, long term evolution (LTE), LTE-advance (LTE-A), code division multiple access (CDMA), wideband CDMA (WCDMA), universal mobile telecommunications system (UMTS), wireless broadband (WiBro), and global system for mobile communications (GSM), as a cellular communication protocol. In addition, the wireless communication may include, for example, short-range communication 164. The short range communication 164 may include at least one of, for example, Wi-Fi, Bluetooth (BT), near field communication (NFC), and global navigation satellite system (GNSS). The GNSS may include at least one of, for example, a GPS, a global navigation satellite system (Glonass), a Beidou navigation satellite system (hereinafter referred to as "Beidou"), and a European global satellite-based navigation system (Galileo), according to a use area, a bandwidth, or the like. Hereinafter, in the present disclosure, the "GPS" may be interchangeably used with the "GNSS". The wired communication may include at least one of, for example, a universal serial bus (USB), a high definition multimedia interface (HDMI), recommended standard 232 (RS-232), and a plain old telephone service (POTS). The network 162 may include at least one of a communication network such as a computer network (e.g., a local area network (LAN) or a wide area network (WAN)), the Internet, and a telephone network.

Each of the first and second external electronic devices 102 and 104 may be of the same or a different type from the electronic device 101. According to an embodiment of the present disclosure, the server 106 may include a group of one or more servers. According to various embodiments of the present disclosure, all or some of the operations performed in the electronic device 101 may be performed in another electronic device or a plurality of electronic devices (for example, the electronic devices 102 and 104 or the server 106). According to an embodiment of the present disclosure, when the electronic device 101 has to perform some functions or services automatically or in response to a request, the electronic device 101 may make a request for performing at least some functions relating thereto to another device (for example, the electronic device 102 or 104 or the server 106) instead of performing the functions or services by itself or in addition. Another electronic apparatus (the electronic devices 102 and 104, or the server 106) may execute the requested functions or the additional functions, and may deliver a result of the execution to the electronic apparatus 101. The electronic device 101 may provide the received result as it is or additionally process the received result and provide the requested functions or services. To achieve this, for example, cloud computing, distributed computing, or client-server computing technology may be used.

Figure 2A:
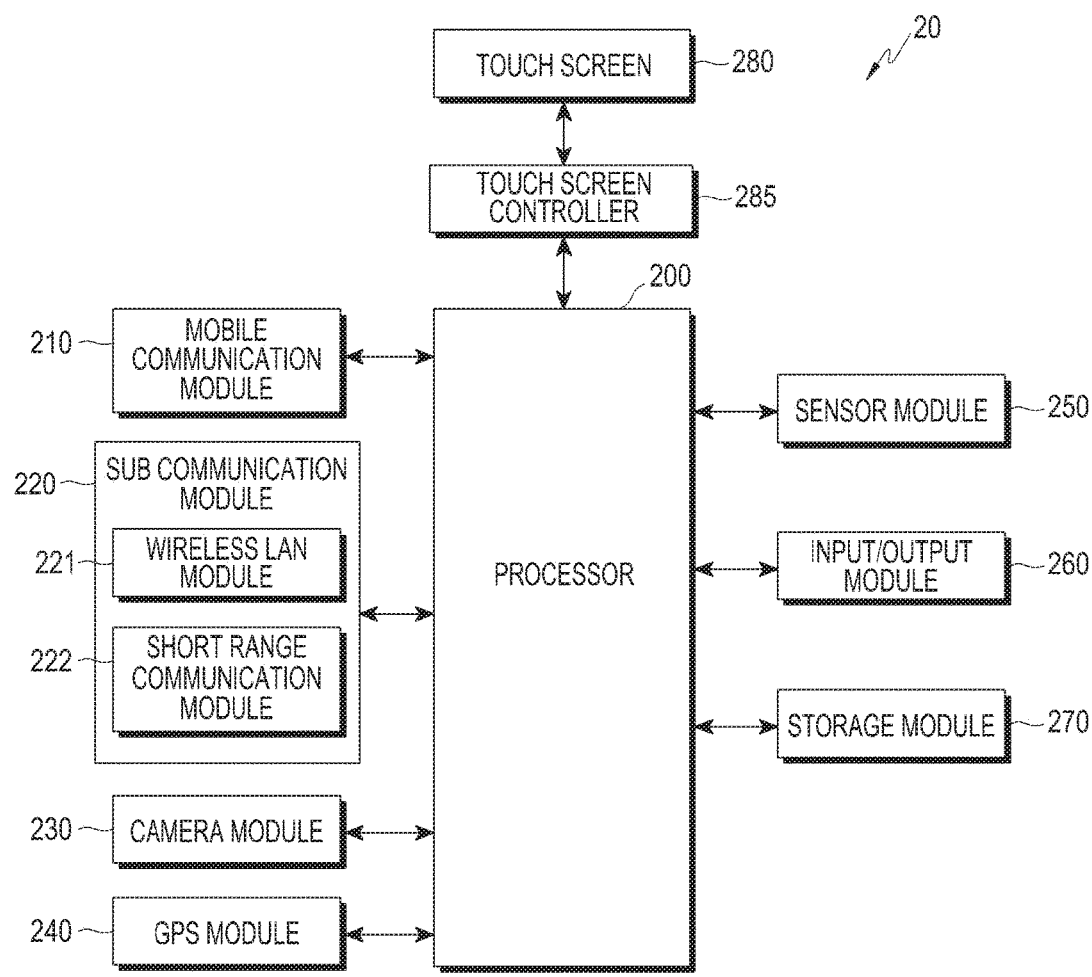
FIGS. 2A to 2C are diagrams illustrating an example of an electronic device according to various embodiments of the present disclosure.
Figure 2B:
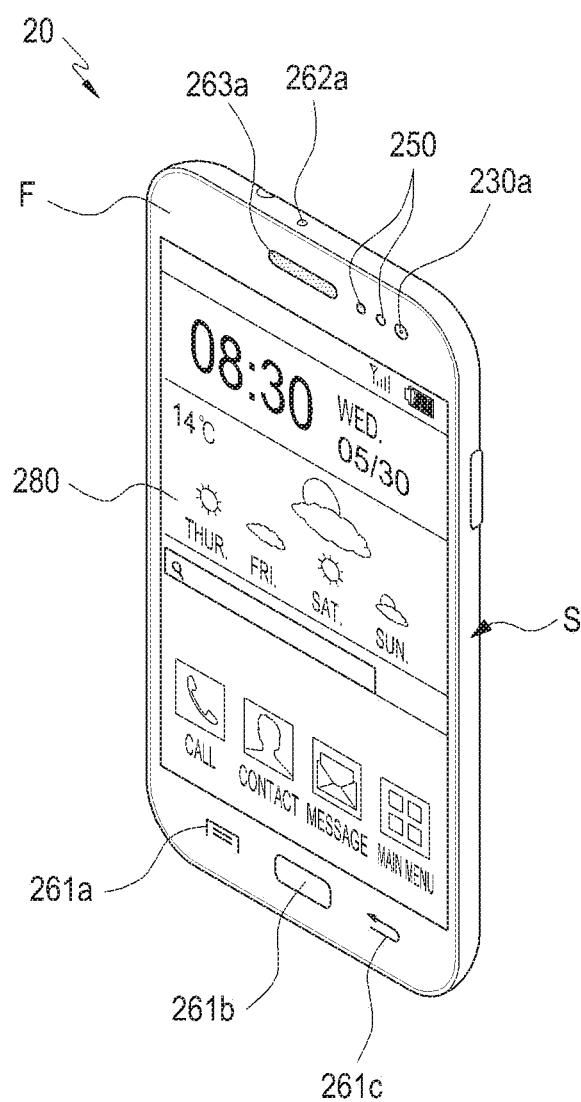
Figure 2C:
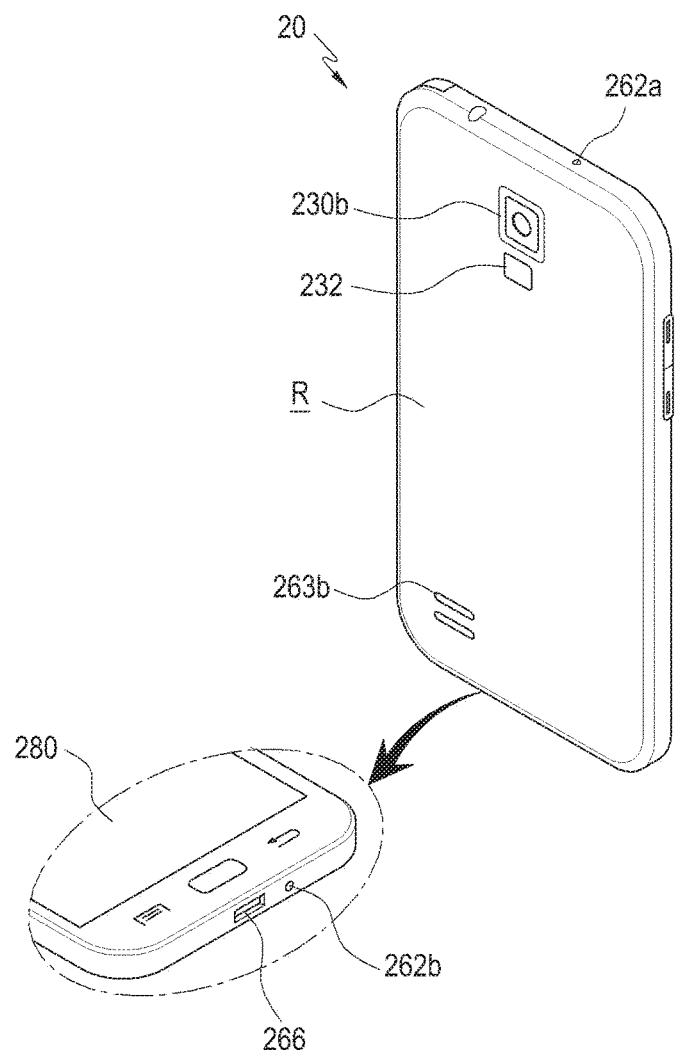

FIGS. 2A to 2C are diagrams illustrating an electronic device according to various embodiments of the present disclosure.

Referring to FIG. 2A, an electronic device 20 according to various embodiments of the present disclosure may include a processor 200, a mobile communication module 210, a sub communication module 220, a camera module 230, a GPS module 240, a sensor module 250, an input/output module 260, and a storage module 270.

The processor 200 may include a CPU, a read only memory (ROM) storing a control program for controlling the electronic device 20, and a random access memory (RAM) used as a memory area for storing a signal or data input from the outside of the electronic device 20 or for an operation performed in the electronic device 20. The CPU, the ROM, and/or the RAM may be connected with each other through internal buses.

The mobile communication module 210 may connect the electronic device 20 to an external device through mobile communication using at least one antenna or a plurality of antennas (not illustrated) under the control of the processor 200. The mobile communication module 210 may transmit/receive a wireless signal for a voice call, a video call, a short message service (SMS), or a multimedia messaging service (MMS) with a portable phone, a smart phone, a tablet PC, or another external device having a telephone number input into the electronic device 20.

The sub communication module 220 may include a wireless LAN module 221 and/or a short range communication module 222. The wireless LAN module 221 may be connected to the Internet at a place at which a wireless AP (not shown) is installed under the control of the processor 200. The wireless local area network (WLAN) module 221 supports a WLAN standard (IEEE802.11x) of the Institute of Electrical and Electronics Engineers (IEEE). The short range communication module 222 may wirelessly establish short range communication with other external electronic devices under the control of the processor 200. The short-range communication scheme may include a BT communication scheme, an infrared data association (IrDA) scheme, a Wi-Fi Direct communication scheme, a NFC scheme, and the like. The electronic device 20 may include at least one of the mobile communication module 210, the wireless LAN module 221, and the short range communication module 222 according to performance. For example, the electronic device 20 may include a combination of the mobile communication module 210, the wireless LAN module 221, and the short range communication module 222 according to performance.

The camera module 230 may include at least one of a first camera 230a and a second camera 230b disposed on a front portion F of the electronic device 20. Further, the first camera 230a or the second camera 230b may include an auxiliary light source (for example, a flash 232) for providing a light quantity necessary for the photographing.

The GPS module 240 may receive radio waves from a plurality of GPS satellites on the earth's orbit, and calculate a location of the electronic device 20 by using a time of arrival from the GPS satellite to the electronic device 20. In the present disclosure, the term "GPS module 240" may be replaced with and referred to as a term "location sensor" as necessary.

The sensor module 250 may measure a physical quantity or may detect an operating state of the electronic device 20, and may convert the measured or detected information into an electrical signal. The sensor module 250 according to various embodiments of the present disclosure may include at least one of, for example, an acceleration sensor, a gyro sensor, a geomagnetic sensor, a magnetic sensor, a luminance sensor, a proximity sensor, a gesture sensor, a grip sensor, and a biometric sensor 337. Additionally or alternatively, the sensor module 250 may include a biometric sensor, for example, an E-nose sensor, an electromyography (EMG) sensor, an electroencephalogram (EEG) sensor, an electrocardiogram (ECG) sensor, an iris sensor, and a finger print sensor, and may recognize the health information about the user using by the biometric sensor. The sensor module 250 may further include a control circuit for controlling at least one sensor included therein.

The input/output module 260 may include at least one of a plurality of buttons 261a, 261b, and 261c, microphones 262a and 262b, speakers 263a and 263b, a vibration motor, a connector 266, and a keypad.

The plurality of buttons 261a, 261b, and 261c may be formed on, for example, a front surface F, a lateral surface S or a rear surface R of a housing of the electronic device 20, and may include at least one of a power/lock button, a volume button, a menu button, a home button, a back button, and a search button.

The microphones 262a and 262b may generate electrical signals by receiving a voice or a sound under the control of the processor 200.

The speakers 263a and 263b may output sounds corresponding to various signals (for example, a wireless signal, a broadcasting signal, a digital audio file, a digital video file, or photography) of the mobile communication module 210, the sub communication module 220, the input/output module 260, or the camera module 230 to the outside of the electronic device 20 under the control of the processor 200. The speakers 263a and 263b may output a sound (for example, a button operation sound or a call connection sound corresponding to a telephone call) corresponding to a function performed by the electronic device 20. One or more of the speakers 263a and 263b may be formed at an appropriate position or appropriate positions of the housing of the apparatus 20.

The vibration motor may convert an electrical signal into a mechanical vibration under the control of the processor 200. For example, when the electronic device 20 in a vibration mode receives a voice call from another external electronic device/other external electronic devices, the vibration motor may be operated. One vibration motor or a plurality of vibration motors may be formed within the housing of the electronic device 20. The vibration motor may be operated in response to a user's touch motion of touching the touch screen display 280 and a successive motion of a touch on the touch screen 280.

The connector 266 may be used as an interface for connecting the electronic device 20 with another external electronic device/other external electronic devices or a power source. The electronic device 20 may transmit data stored in the storage module 270 of the electronic device 20 to another external electronic device/other external electronic devices or receive data from another external electronic device/other external electronic devices through a wired cable connected to the connector 266 under the control of the processor 200. In this case, another external electronic device/other external electronic devices may be docking stations, and the data may be an input signal transmitted from an external input device, for example, a mouse and a keyboard. Further, the electronic device 20 may receive power from a power source through a wired cable connected to the connector 266 or charge a battery by using the power source.

The keypad may receive a key input from the user for the control of the electronic device 20. The keypad may include a physical keypad provided in the electronic device 20, or a virtual keypad displayed on the touch screen 280. The physical keypad provided at the electronic device 20 may be excluded according to performance or a structure of the electronic device 20.

An earphone may be inserted into an earphone connecting jack and may be connected to the electronic device 20.

The storage module 270 may store signals or data input/output in response to the operations of the mobile communication module 210, the sub communication module 220, the camera module 230, the GPS module 240, the sensor module 250, the input/output module 260, the storage module 270, and the touch screen 280 under the control of the processor 200. The storage module 270 may store a control program and applications for controlling the electronic device 20 or the processor 200.

The touch screen 280 may provide a user with a user interface (UI) corresponding to various services (e.g., a voice call, data transmission, broadcasting, and photographing) The touch screen 280 may transmit an analog signal corresponding to at least one touch, which is input to the UI, to a touch screen controller 285. The touch screen 280 may receive at least one touch through a user's body part (e.g., fingers including a thumb) or a touchable input means (e.g., a stylus pen). In addition, the touch screen 280 may receive an input of continuous movement of one touch among one or more touches. The touch screen 280 may transmit an analog signal corresponding to the successive motions of the input touch to the touch screen controller 285. In the present disclosure, the touch is not limited to a contact of the touch screen 280 with a user's body part or a touchable input means, and may include a non-contact. The detectable interval of the touch screen 280 may be changed according to a capability or structure of the electronic device 20. The touch screen 280 may be implemented, for example, in a resistive type, a capacitive type, an infrared (IR) type, or an acoustic wave type.

The touch screen controller 285 may convert an analog signal received from the touch screen 280 into a digital signal (for example, X and Y coordinates) and transmit the converted digital signal to the processor 200. The processor 200 may control the touch screen 280 by using a digital signal received from the touch screen controller 285. For example, the processor 200 may allow a shortcut icon displayed on the touch screen 280 to be selected or execute the shortcut icon in response to the touch. Further, the function(s) or the operation(s) performed by the touch screen controller 285 may also be performed by the processor 200.

Referring to FIGS. 2B and 2C, the electronic device 20 may include an external housing. The touch screen 280 may be provided on the front surface F of the electronic device 20. A home button, a menu button, and a back button may be arranged on the lower part of the touch screen 280. Further, the first camera 230a and the sensor module 250 (for example, the luminance sensor and the proximity sensor) may be provided on the front surface F of the electronic device 20. The second camera 230b, a flash 254, and a speaker module 224 may be provided on the rear surface R of the electronic device 20. A power/reset button, a volume button, a terrestrial digital multimedia broadcasting (DMB) antenna for receiving a broadcast, one or more microphones, and the like may be provided on the lateral surface S (that is, the lateral side of the external housing) of the electronic device 20. A connector 226 and the microphone module 222 may be provided at a lower end of the electronic device 20.

A plurality of electrodes may be provided at the connector 226, and may be wired connected with the external device through the connector 226.

Figure 3:
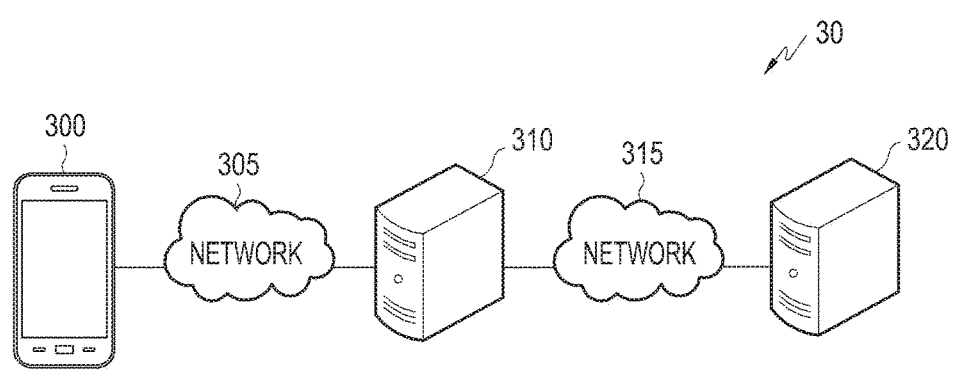
FIG. 3 is a diagram illustrating an example of an emergency rescue system according to various embodiments of the present disclosure.

FIG. 3 is a diagram illustrating an example of an emergency rescue system according to various embodiments of the present disclosure.

Referring to FIG. 3, an example of an emergency rescue system 30 according to various embodiments of the present disclosure may include an electronic device 300 used by a help requester, a relay server 310 connected with the electronic device 300 through networks 305 and 315, such as a cellular communication network and/or a data communication network, and an external electronic device 320 (for example, a server of a rescue organization) receiving a help request signal from the electronic device 300 or the relay server 310. The electronic device 300, the relay server 310, and the external electronic device 320 may be connected with each other through the networks 305 and 315. According to various embodiments of the present disclosure, the electronic device 300 may be connected with a sub electronic device (for example, a wearable device worn on a part of a body of the help requester) through wireless communication. According to various embodiments of the present disclosure, the sub electronic device may include various sensors for obtaining health information about the help requester. For the convenience of description, the external electronic device 320 may be particularly divided into and referred to as a "first external electronic device" and a "second external electronic device" in the present disclosure. The "first external electronic device" may mean a terminal used by a server of a rescue organization (for example, a fire station and a police office), or a terminal (a terminal used (or carried) by a rescuer belonging to the rescue organization) of the rescue organization. The "second external electronic device" may mean a portable terminal (for example, the terminal of parents of the help requester and terminals of friends of the help requester) indicated by an identification number (for example, a telephone number) predesignated by the help requester. According to various embodiments of the present disclosure, the "health information" may be replaced with and referred to as various terms, for example, "health information," "body information," and a "body state."

According to various embodiments of the present disclosure, the help requester may send an emergency call (for example, a 119 call) through the electronic device 300 in order to notify the rescue organization of his/her emergency situation. In the present disclosure, the "emergency situation" may mean a case where the help requester needs to notify the rescue organization of his/her emergency situation due to a sudden or significant change (for example, a sharp increase or decrease in a heartbeat rate of the help requester) in his/her health information. Further, in the present disclosure, an "emergency mode" may mean an operation mode of the electronic device 300 for notifying the rescue organization of the current state of the help requester. For example, when a processor (for example, the processor 200) of the electronic device 300 receives an emergency call sending request from the help requester, the processor of the electronic device 300 may control an operation mode of the electronic device 300 to be changed into the "emergency mode" from a reception time of the emergency call sending request. Otherwise, when the health information (for example, the heartbeat rate and a temperature of the help requester) about the help requester obtained through the electronic device 300 or the wearable device passes a threshold value, the processor of the electronic device 300 may control the operation mode of the electronic device 300 to be changed into the emergency mode. The emergency mode may be controlled to be terminated when, for example, a predetermined time elapses after the change into the emergency mode or the health information about the help requester returns to a normal range. The processor may control the operation mode of the electronic device 300 to be changed to a general mode when the emergency mode is terminated. In the general mode, the health information about the help requester may not be transmitted to the rescue organization.

According to various embodiments of the present disclosure, the electronic device 300 may receive a help request for the rescue organization from the help requester. As described above, the help request may include, for example, the emergency call sending request for the rescue organization. When the emergency call sending request is received, the processor of the electronic device 300 may control the operation mode of the electronic device 300 to be changed into the emergency mode. When the operation mode of the electronic device 300 is changed into the emergency mode, the electronic device 300 may detect the current location of the electronic device 300 to be transmitted to the rescue organization, generate location information about the detected current location, and transmit the generated location information to the external electronic device 320. The generated location information may be transmitted to the external electronic device 320 through the relay server 310. The function or the operation of detecting the current location of the electronic device 300 may be performed by, for example, a GPS module (for example, the GPS module 240) provided at the electronic device 300 or the wearable device.

According to various embodiments of the present disclosure, the electronic device 300 may transmit the location information to the external electronic device 320, and then transmit the health information about the help request to the external electronic device 320. According to various embodiments of the present disclosure, the function or the operation of transmitting the health information about the help request to the external electronic device 320 may be performed based on a request (which may be referred to as the term "health information providing request" in the present disclosure) of the external electronic device 320. Otherwise, when there is no request from the external electronic device 320, the electronic device 300 may transmit the location information to the external electronic device 320. According to various embodiments of the present disclosure, the health information providing request may be performed by the external electronic device 320, or may be performed by the relay server 310. According to various embodiments of the present disclosure, the health information about the help requester may contain information (for example, the current heartbeat rate and a temperature of the help requester) obtained by the electronic device 300 or the sensor module (for example, the sensor module 250) of the wearable device. Otherwise, the health information may contain health information (for example, information about a currently taken medication of the help requester) related to the help requester pre-stored in the electronic device 300. As described above, according to various embodiments of the present disclosure, it is possible to enable the rescuer to rapidly determine a current body state of the help requester by transmitting the health information about the help requester to the rescuer as well as the location information, thereby rapidly performing a rescue activity.

For example, the sensor module provided at the electronic device 300 or the wearable device may measure a physical quantity or detect an operation state of the electronic device 300 or the wearable device, and convert the measured or detected information into an electrical signal. The sensor module may include at least one of, for example, a gesture sensor, a gyro sensor, an atmospheric pressure sensor, a magnetic sensor, an acceleration sensor, a grip sensor, a proximity sensor, a color sensor (for example, an red, green, and blue (RGB) sensor), a biometric sensor, a temperature/humidity sensor, an illuminance sensor, and an ultra violet (UV) sensor. Additionally or alternatively, the sensor module may include, for example, an E-nose sensor, an EMG sensor, an EEG sensor, an ECG sensor, an IR sensor, an iris sensor, and/or a fingerprint sensor. The sensor module may further include a control circuit for controlling at least one sensor included therein. In some embodiments of the present disclosure, the electronic device 300 or the wearable device may further include a processor configured to control the sensor module as a part of the processor 120 or separately, and may control the sensor module while the processor is in a sleep state.

The relay server 310 may receive various signals transmitted from the electronic device 300, and transmit the received signals to the external electronic device 320. The 310 may be connected with the electronic device 300 and the external electronic device 320 through the networks 305 and 315, such as a cellular communication network and a wired/wireless data communication network.

The external electronic device 320 may include a server managed (that is, possessed or located) by the rescue organization (for example, a fire station) from which the help requester requests the help. However, in FIG. 3, the "server" is illustrated as the various embodiments of the present disclosure, but is illustrative. According to various embodiments of the present disclosure, the 302 may additionally or alternatively include at least one of a smart phone, a tablet PC, a mobile phone, a video phone, an e-book reader, a desktop PC, a laptop PC, and a netbook computer. Further, the external electronic device 320 may include other electronic devices (for example, portable terminals possessed by acquaintances of the help requester) predesignated by the help requester.

FIG. 4A is a diagram for describing an instruction stored in a reserved field according to various embodiments of the present disclosure applied in a synchronous IS-801 protocol.

Referring to FIG. 4A, in an embodiment according to the synchronous location information providing standard of IS-801, in which the network (for example, the networks 305 and 315) of the emergency rescue system (for example, the emergency rescue system 30) according to various embodiments of the present disclosure, a case where an instruction requesting health information about the help requester in the emergency mode is added to a reserved field is illustrated. As illustrated in FIG. 4A, the instruction stored in the reserved field may include an instruction having the same form as that of the instruction providing location information according to the IS-801 standard. Further, according to various embodiments of the present disclosure, in addition to the location information and the health information, an instruction transmitting information on various physical quantities detected by the sensor module (for example, the sensor module 250) of the electronic device 300 to the external electronic device 320 may be further included in the reserved field. The term "instruction" referred in the present disclosure may also be replaced with and used as the term "command" according to various embodiments of the present disclosure.

Figure 4B:
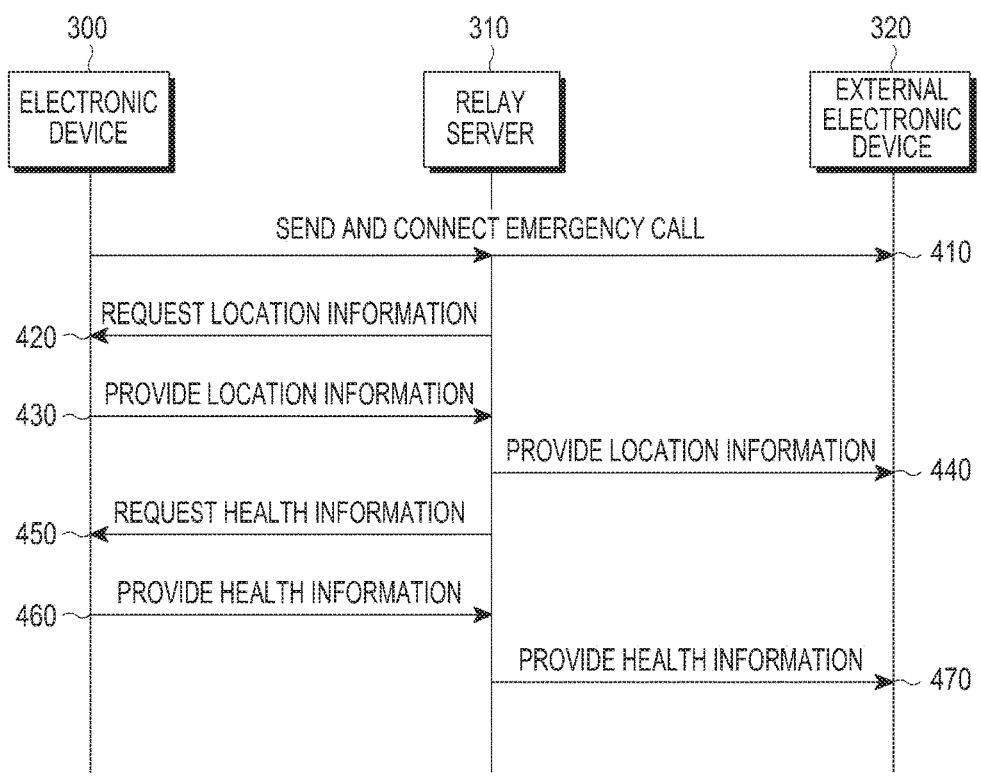
FIG. 4B is a diagram for describing an operating method of the emergency rescue system according to various embodiments of the present disclosure applied in the synchronous IS-801 protocol.

FIG. 4B is a diagram for describing an operating method of the emergency rescue system according to various embodiments of the present disclosure applied in the synchronous IS-801 protocol.

Referring to FIG. 4B, the help requester may request help from the rescue organization through the electronic device 300 in operation 410. The help request may include an emergency call, for example, a 119 call. When the emergency call is connected between the help requester and the rescue organization, the relay server 310 may transmit a request for obtaining information on the current location of the help requester in operation 420. The electronic device 300 may obtain the location information about the electronic device 300 according to a request of the relay server 310 and transmit the obtained location information to the relay server 310 in operation 430. The relay server 310 may transmit the location information about the electronic device 300 to the external electronic device 320 in operation 440. The electronic device 300 may provide the location information about the electronic device 300, and then receive the request for providing health information about the help requester in operation 450. When the electronic device 300 receives the request for providing the health information, the electronic device 300 may provide the health information about the help requester to the relay server 310 and/or the external electronic device 320 according to the request in operations 460 and 470. The health information may contain at least one of, for example, a heartbeat rate of the help requester, a blood pressure of the help requester, a blood sugar level of the help requester, a temperature of the help requester, recent administration information of the help requester, a recent hospital visit history of the help requester, and a medical record of the help requester. The health information may contain information detected through the electronic device 300 or a sub electronic device connected through wireless communication with the electronic device 300, and information pre-stored in the electronic device 300 by the help requester. According to various embodiments of the present disclosure, the rescue organization may rescue the help requester based on the location information and the health information provided from the electronic device 300.

According to various embodiments of the present disclosure, operations 420 to 470 illustrated in FIG. 4B may be performed in one session. Further, the relay server 310 determining the position of the user may include, for example, a position determination entity (PDE). The location information about the electronic device 300 may be obtained by, for example, the GPS module 240.

According to various embodiments of the present disclosure, the location information and the health information according to various embodiments of the present disclosure may be transmitted based on the asynchronous LTE positioning protocol (LPP). Table 1 below represents an example of an instruction for transmitting the health information about the help requester according to various embodiments of the present disclosure to the external electronic device 320.

TABLE 1

ASN1 START
LPP-MessageBody ::= CHOICE {
c1 CHOICE {
requestCapabilities RequestCapabilities,
provideCapabilities ProvideCapabilities, TABLE 1-continued

```
        requestAssistanceData RequestAssistanceData,
        provideAssistanceData ProvideAssistanceData,
        requestLocationInformation RequestLocationInformation,
        provideLocationInformation ProvideLocationInformation,
        abort Abort,
        error Error,
        ========== Definition of spare and health
service===========================
        spare7 NULL, => requestHealthCapabilities
        RequestHealthCapabilities,
        spare6 NULL, => provideHealthCapabilities
        ProvideHealthCapabilities
        spare5 NULL, => requestHealthData RequestHealthAData
        spare4 NULL, => provideHealthData ProvideHealthAData
        spare3 NULL,
        spare2 NULL,
        spare1 NULL,
        spare0 NULL
        }, messageClassExtension SEQUENCE { }
        }
        -- ASN1 STOP
```

Referring to Table 1, in the asynchronous LPP, the additional instruction may be additionally defined as a total of seven spares, spare1 to spare7. In the instruction, in order to provide the health information to the rescue organization, the instructions defined from spare4 to spare7 are illustrated.

Figure 5:
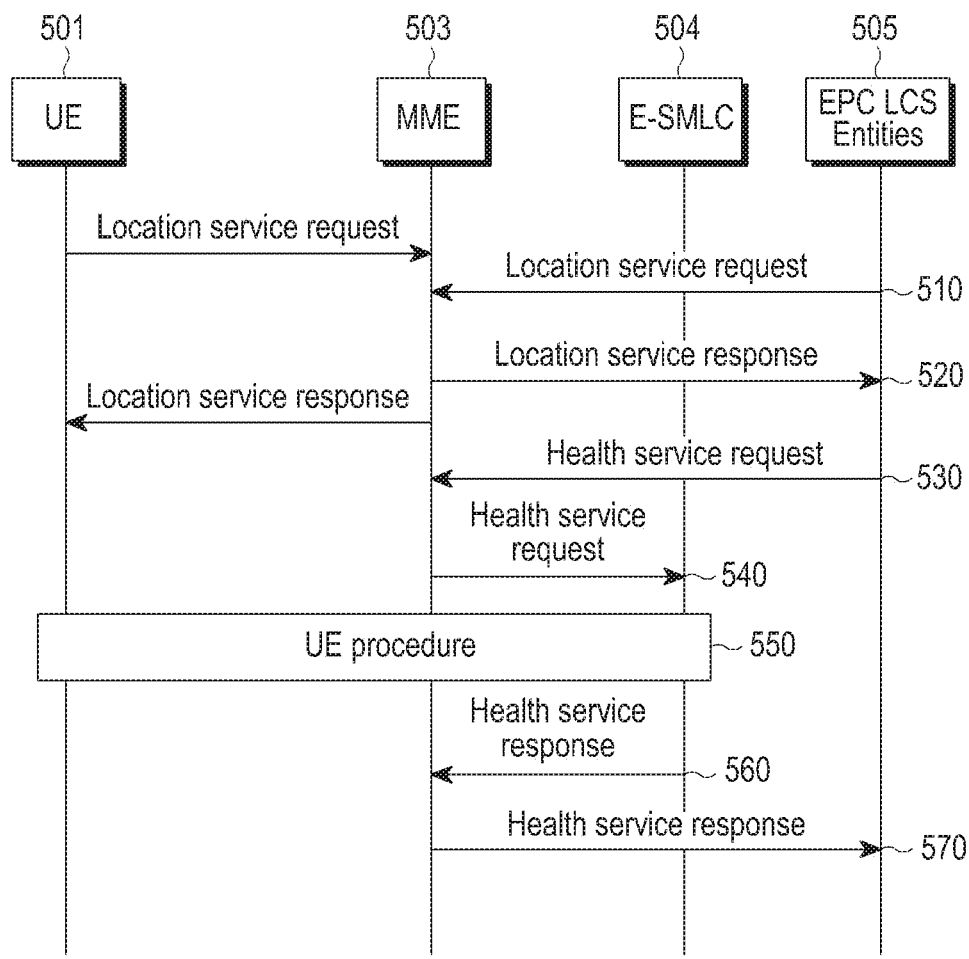
FIG. 5 is a diagram for describing an operating method of the emergency rescue system according to various embodiments of the present disclosure applied in an asynchronous long-term evolution (LTE) positioning protocol (LPP)

FIG. 5 is a diagram for describing an operating method of the emergency rescue system according to various embodiments of the present disclosure applied in the asynchronous LPP.

Referring to FIG. 5, after an emergency call is connected, a mobility management entity (MME) 503 may receive a request for providing the current location of the electronic device 300 (for example, a user equipment (UE) 501) to the relay server 310 (for example, an E-SMLC 504) and/or the external electronic device 320 (for example, EPC LCS entities 505) in operation 510. According to the request, the MME 503 may provide the current location of the UE 501 to the UE 501 and the EPC LCS entities 505 in operation 520. The MME 503 may receive a request for receiving health information about the help requester from the EPC LCS entities 505 in operation 530. The MME 503 may transmit the request received through the operation 530 to the E-SMLC 504 in operation 540. In a UE procedure 550 illustrated in FIG. 5, information on a capability for obtaining the health information about the UE 501 may be transceived between the UE 501 and the E-SMLC 504. The term "capability" means, for example, whether the UE 501 is capable of performing a specific function/operation, and may be replaced with and used as the term "serviceability". The MME 503 may receive a response corresponding to the operation 540 and/or the operation 550 from the E-SMLC 504 in operation 560. The MME 503 may obtain the health information about the help requester through the sensor module provided at the UE 501, or provide at least one element of information among recent medical treatment information of the help requester, recent administration information of the help requester, and recent medicine purchase information of the help requester stored in the UE 501 to the EPC LCS entities 505 in operation 570. According to various embodiments of the present disclosure, at least some of the functions or the operations performed by the MME 503 may also be performed by the UE 501.

Figure 6:
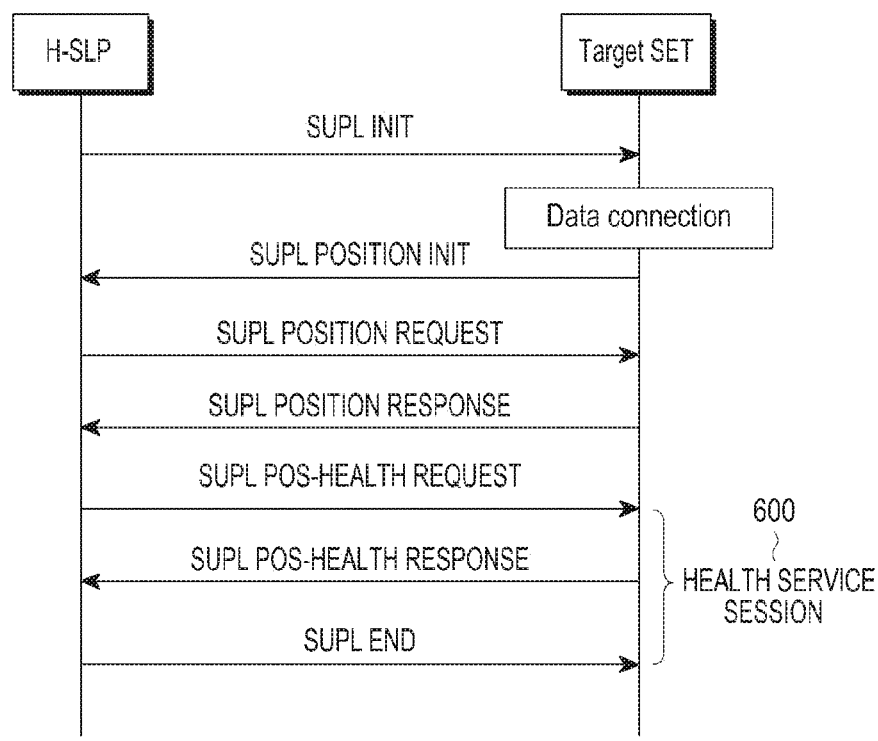
FIG. 6 is a diagram for describing an operating method of the emergency rescue system according to various embodiments of the present disclosure applied in an Open Mobile Alliance (OMA)-Secure User Plane Location (SUPL)

FIG. 6 is a diagram for describing an operating method of the emergency rescue system according to various embodiments of the present disclosure applied in an Open Mobile Alliance (OMA)-Secure User Plane Location (SUPL).

When the emergency rescue system is operated in the OMA-SUPL protocol, in order to provide health information about the help requester to the external electronic device 320, the health information about the help requester may be provided by additionally setting a health session 600 before SUPL_END, and then an entire operation procedure of the emergency rescue system may be terminated according to the SUPL_END instruction.

Figure 7A:
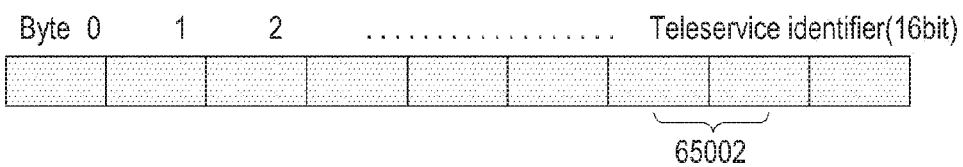
FIG. 7A is a diagram for describing a function/operation, in which an short message service (SMS) teleservice identifier (ID) is newly defined for transmitting health information according to various embodiments of the present disclosure.

FIG. 7A is a diagram for describing a function/operation, in which an SMS teleservice identifier (ID) is defined for transmitting health information according to various embodiments of the present disclosure.

The IS-801 standard for the synchronous location service may generally use the SMS teleservice ID 65001. However, according to various embodiments of the present disclosure, for example, as described with reference to FIG. 4A, a method of newly defining a teleservice without using the reserved field may be available. The teleservice ID is 16 bits on the SMS, and may be defined by 0 to 65535. For example, an ID for providing the health information about the help requester may be defined by 65002. When the ID for providing the health information about the help requester is defined by 65002, an instruction and a response, which are exchangeable through the defined 65002, may be defined. The same description related to the provision of the location information and the health information described in the IS-801 may be applied to subsequent operations. In the present disclosure, the Teleservice ID 65002 may be referred to as "TIA 802" for the convenience of description.

Figure 7B:
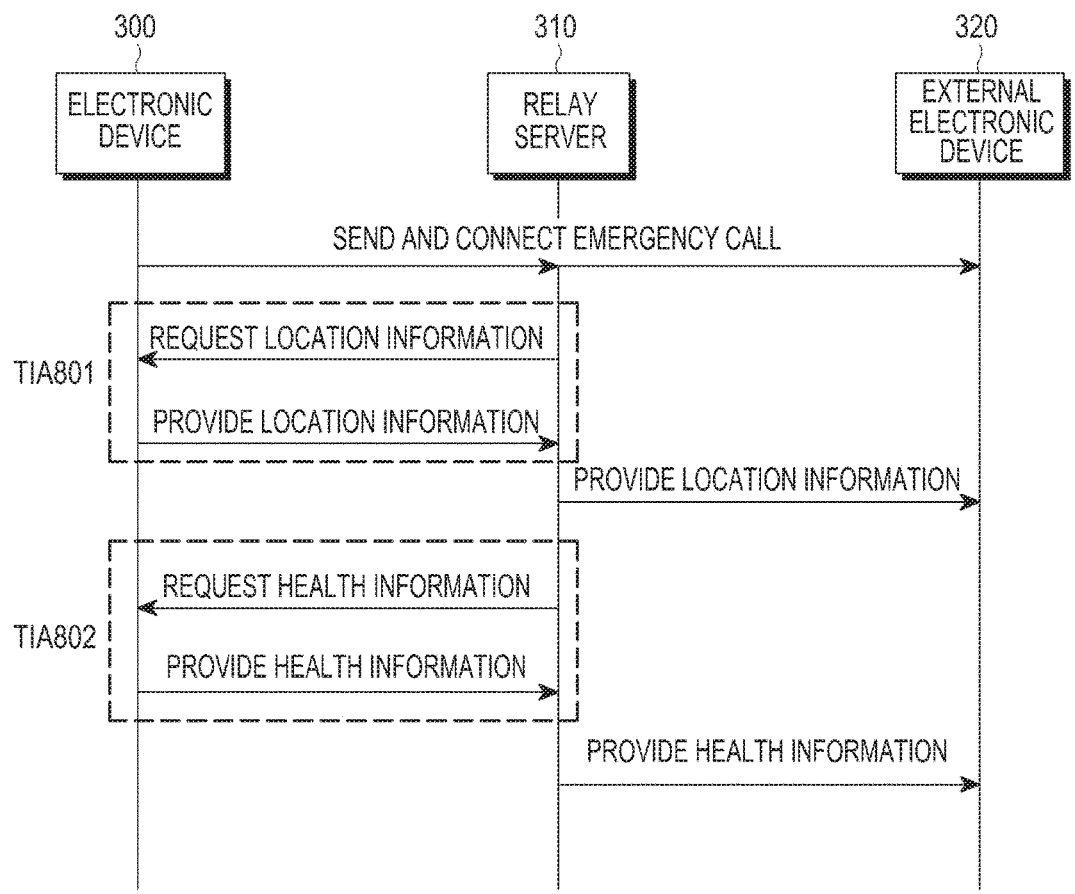
FIG. 7B is a diagram for describing an embodiment of the present disclosure, in which health information according to various embodiments of the present disclosure is transmitted to an external electronic device(s) through the newly defined SMS teleservice ID.

FIG. 7B is a diagram for describing an embodiment of the present disclosure, in which health information about a help requester according to various embodiments of the present disclosure is transmitted to an external electronic device(s) through the SMS teleservice ID defined as illustrated in FIG. 7A.

Referring to FIG. 7B, the Teleservice 65002 (TIA 802) session described with reference to FIG. 7A may be set after a session for providing the location information about the help requester is set. Here, the session (that is, the "TIA 802" session) for providing the health information about the help requester to the external electronic device 320 may be different from a session (that is, a "TIA 801" session) for providing the location information about the help requester. This may be different from the embodiment (that is, the embodiment of the present disclosure, in which both the location information and the health information are transmitted through the "TIA 801" session), in which the reserved field described with reference to FIGS. 4A and 4B is used. In addition, in relation to FIG. 7B, the description related to FIG. 4B may be equally applied within a non-contracted range.

According to various embodiments of the present disclosure, the health information may be provided to the external electronic device 320 through the LHP defined based on the asynchronous LPP, and an example of the instruction for performing the function or the operation is represented in Table 2 below.

TABLE 2

```
-- ASN1 START
LHP-MessageBody ::= CHOICE {
c1 CHOICE {
requestCapabilities RequestCapabilities,
provideCapabilities ProvideCapabilities
requestHealthInformation RequestHealthInformation,
provideHealthInformation ProvideHealthInformation,
```

TABLE 2-continued

```
    abort Abort,
    error Error,
    spare9 NULL,
    spare8 NULL,
    spare7 NULL,
    spare6 NULL,
    spare5 NULL,
    spare4 NULL,
    spare3 NULL,
    spare2 NULL,
    spare1 NULL,
    spare0 NULL
  }, messageClassExtension SEQUENCE { }
  }
-- ASN1 STOP
```

Figure 8:
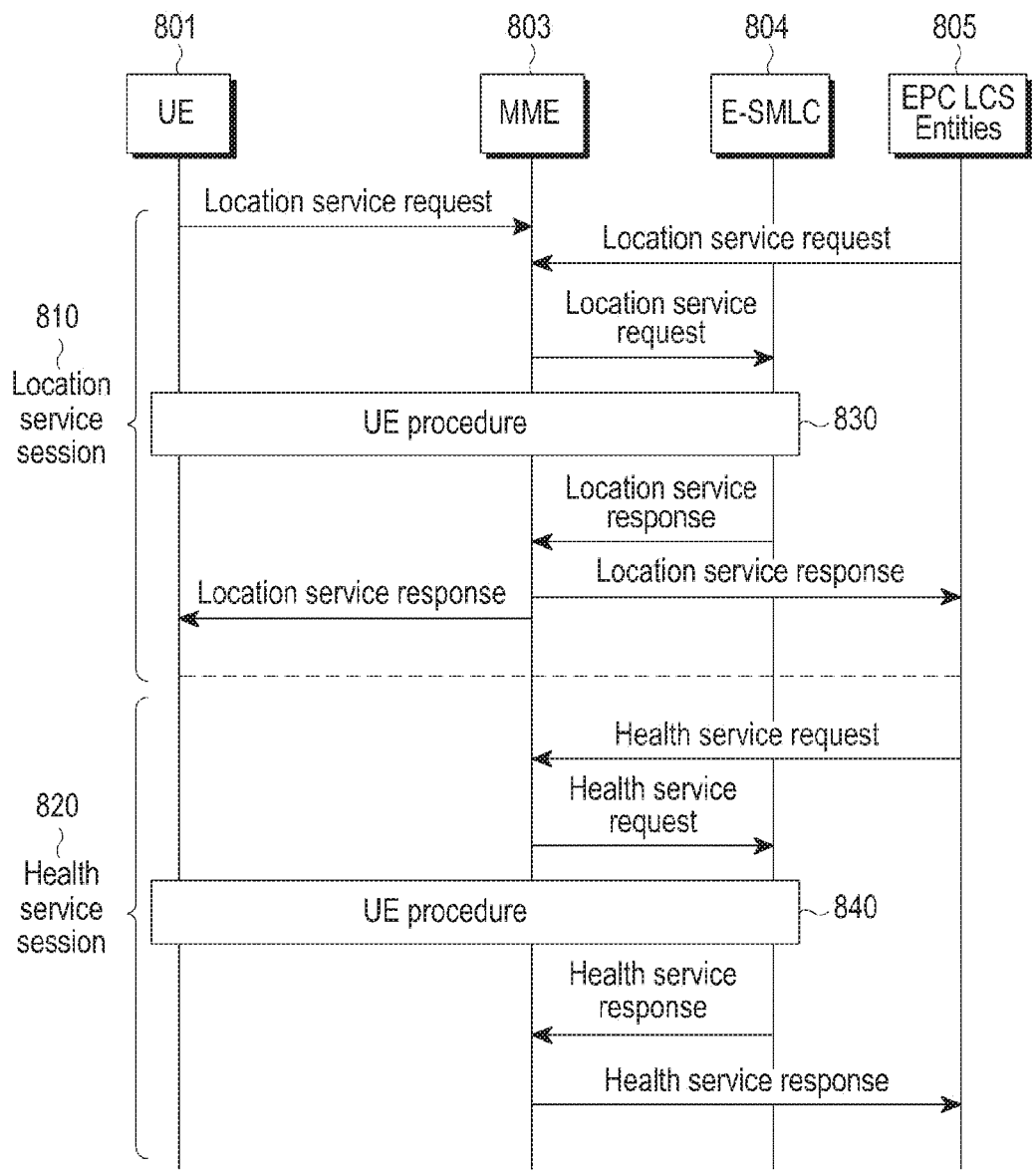
FIG. 8 is a diagram for describing an embodiment of the present disclosure, in which the emergency rescue system according to various embodiments of the present disclosure is operated based on a newly defined link-layer header protection (LHP) protocol.

FIG. 8 is a diagram for describing an embodiment of the present disclosure, in which the emergency rescue system according to various embodiments of the present disclosure is operated based on the LHP.

Referring to FIG. 8, UE procedures 830 and 840 may be operated in different sessions, respectively. The UE 801 or the MME 803 may provide health information about the help requester to an E-SMLC 804 through the SMS teleservice ID or the LHP, which have been described with reference to FIGS. 7A and 7B, by the UE procedure 840 of a health service session 820 illustrated in FIG. 8. According to a request, the MME 803 may provide the current location of the UE 801 to the UE 501 and the EPC LCS entities 805 in location service session 810. Further, unlike the illustration of FIG. 5, the provision of the location information about the electronic device 300 (for example, the UE 801) and the provision of the health information about the help requester are performed in separate sessions, so that the UE procedures 830 and 840 may also be performed in separate sections (for example, a location service session 810 and the health service session 820), respectively. In addition, in relation to FIG. 8, the description related to FIG. 5 may be equally applied within a non-contracted range.

Figure 9:
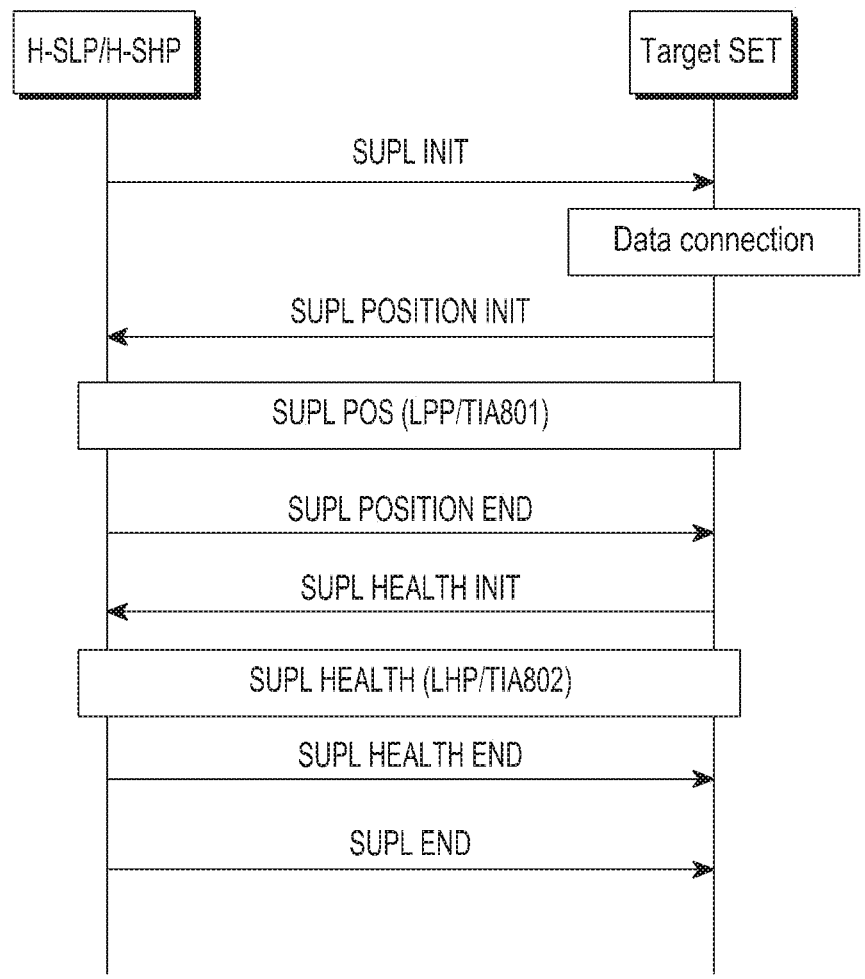
FIG. 9 is a diagram for describing an embodiment of the present disclosure, in which the emergency rescue system according to various embodiments of the present disclosure is operated in the OMA-SPUL based on the newly defined SMS teleservice ID and the newly defined LHP.

FIG. 9 is a diagram for describing an embodiment of the present disclosure, in which the emergency rescue system according to various embodiments of the present disclosure is operated in the OMA-SPUL based on the SMS teleservice ID or the LHP described with reference to FIGS. 7A and 7B.

The OMA may include both a synchronous protocol and an asynchronous protocol. Accordingly, data formats of SUPL_POS and SUPL_HEALTH may be determined according to the kind of operated network. According to various embodiments of the present disclosure, as illustrated in FIG. 9, the health information may be transmitted to the external electronic device 320 (for example, a target SET) through the TIA 802 and the LPH.

Figure 10:
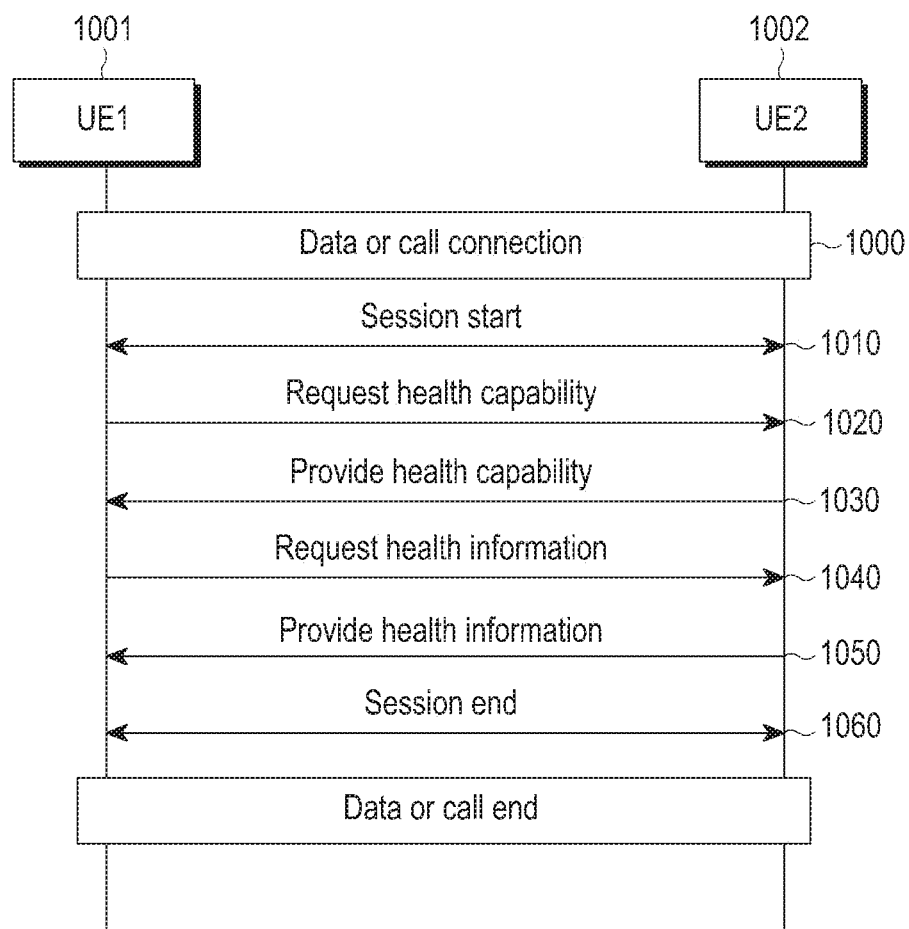
FIG. 10 is a diagram for describing an embodiment of the present disclosure, in which the emergency rescue system according to various embodiments of the present disclosure is operated between personal user terminals based on the newly defined SMS teleservice ID and the newly defined LHP.

FIG. 10 is a diagram for describing an embodiment of the present disclosure, in which the emergency rescue system according to various embodiments of the present disclosure is operated between personal user terminals based on the SMS teleservice ID or the LHP described with reference to FIGS. 7A and 7B.

According to various embodiments of the present disclosure, health information may be exchanged man to man based on the SMS teleservice ID or the LHP described with reference to FIGS. 7A and 7B. Referring to FIG. 10, the electronic device 300 (for example, a "UE 2 1002" of FIG. 10) may send an emergency call to the external electronic device 320 (a "UE 1 1001" in FIG. 10). When the external electronic device 1001 receives the emergency call in operation 1000, the electronic device 1002 may change an operation mode of the electronic device 1002 to an emergency mode. The electronic device 1002 may set a session for transmitting health information about the help requester according to the change of the operation mode in operation 1010. The external electronic device 1001 may request a confirmation of whether it is possible to obtain the health information about the help requester, that is, a health capability, from the electronic device 1002 in operation 1020. The electronic device 1002 may transmit a response to the request for the confirmation of whether it is possible to obtain the health information about the help requester to the external electronic device 1001 according to the request for the health capability in operation 1030. The external electronic device 1001 may request a transmission of current health information about the help requester detected by the electronic device 1002 or health information pre-stored in the electronic device 1002 according to the response to the request for the confirmation of the health capability received from the electronic device 1002 in operation 1040. The electronic device 1002 may transmit the health information detected by the electronic device 1002 or pre-stored in the electronic device 1002 to the external electronic device 1001 according to the request for the transmission of the health information in operation 1050. When the health information is transmitted, the electronic device 1002 may terminate the set session in operation 1060. According to various embodiments of the present disclosure, according to the illustration of FIG. 10, the health information transmitted through the session may be transmitted based on the "TIA 802" or the LHP.

According to various embodiments of the present disclosure, the processor 200 may set a first session for transmitting the location information and the health information to the first external electronic device.

According to various embodiments of the present disclosure, the processor 200 may control the health information to be transmitted to the first external electronic device through the set first session according to the instruction for transmitting the health information designated in the reserved field of the synchronous IS-801 standard.

According to various embodiments of the present disclosure, the processor 200 may control the health information to be transmitted to the first external electronic device through the set first session according to the instruction for transmitting the health information designated in the spare command (that is, the spare instruction) of the asynchronous LPP.

According to various embodiments of the present disclosure, the processor 200 may control the health information to be transmitted to the first external electronic device according to the instruction for transmitting the health information to the first external electronic device before the SUPL_END according to the OMA-SUPL standard.

According to various embodiments of the present disclosure, the processor 200 may control a second session for transmitting the location information to the first external electronic device to be set and a third session for transmitting the health information to the first external electronic device to be set.

According to various embodiments of the present disclosure, teleservice IDs of the second session and the third session according to the synchronous IS-801 standard may be different from each other.

According to various embodiments of the present disclosure, the processor 200 may control the health information to be transmitted to the first external electronic device through the third session set according to the synchronous LHP.

According to various embodiments of the present disclosure, the second session and the third session may include the session defined under the OMA-SUPL standard, and the processor 200 may control the health information to be transmitted to the first external electronic device through the third session after the termination of the second session.

According to various embodiments of the present disclosure, the second session and the third session may include a session for direct communication with the first external electronic device.

According to various embodiments of the present disclosure, when the processor 200 enters the emergency mode, the processor 200 may control the location information and the health information to be transmitted to the first external electronic device according to a predetermined priority.

According to various embodiments of the present disclosure, when the processor 200 enters the emergency mode, the processor 200 may control a guidance message pre-stored in the electronic device in relation to the health information to be transmitted to the first external electronic device.

According to various embodiments of the present disclosure, when the processor 200 enters the emergency mode, the processor 200 may control additional information obtained by the electronic device 300 to be transmitted to the first external electronic device together with the location information and the health information.

According to various embodiments of the present disclosure, the additional information may contain at least one element of information among a temperature around the electronic device 300, a name, a telephone number, a job, and a family relation of a predesignated user.

According to various embodiments of the present disclosure, the processor 200 may control a request message requesting a display of the location information and the health information, which are transmitted to the first external electronic device, for a predetermined time to be transmitted to the external electronic device.

According to various embodiments of the present disclosure, when the processor 200 receives a unique ID for receiving the location information and the health information from the second external electronic device, the processor 200 may control the location information and the health information to be transmitted to the second external electronic device.

According to various embodiments of the present disclosure, the request for the change into the emergency mode may include a call sending request for a predesignated emergency phone number.

Figure 11A:
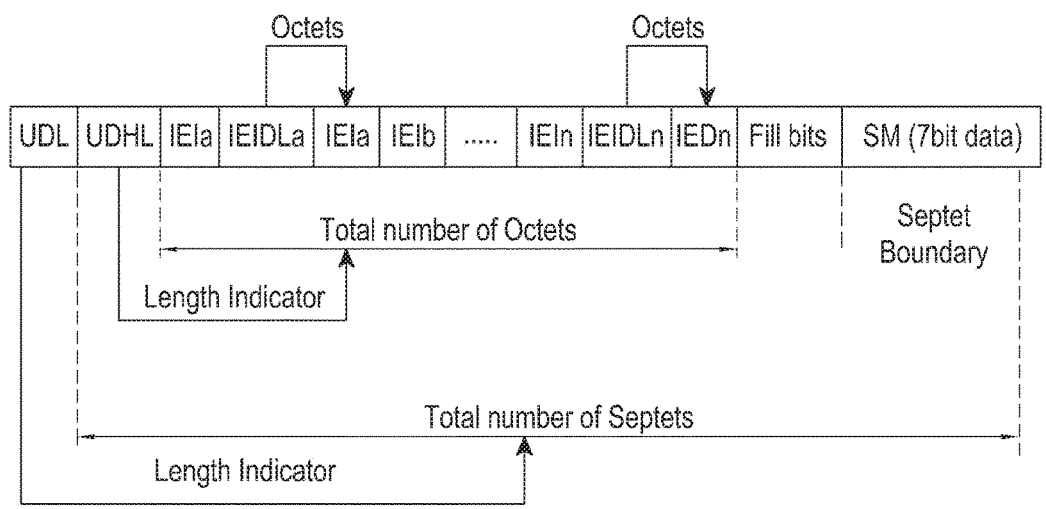
FIG. 11A is a diagram for describing TP-User data according to the 3rd generation partnership project (3GPP) SMS standard according to various embodiments of the present disclosure.

FIG. 11A is a diagram for describing TP-user data according to the 3GPP SMS standard according to various embodiments of the present disclosure, and FIG. 11B is a diagram for an information element identifier (IEI) field among the fields illustrated in FIG. 11A according to various embodiments of the present disclosure.

Referring to FIGS. 11A and 11B, when the IEI field is designated as 0x04 or 0x05, information element data (IED) may designate an application port.

FIG. 11C is a diagram for a Wireless Application Protocol (WAP) Push port 2948 designated as an MMS notification port in an OMA device management (DM).

According to various embodiments of the present disclosure, the designated application port may use TCP/UDP port information (for example, http://www.iana/org/assignments/service-names-port-numbers/service-names-port-numbers.txt) defined in the internet assigned numbers authority (IRNA). In the OMA DM, the WAP Push port may be used as the MMS notification port, and thus, when the application port is designated as the WAP Push Port 2948, the application port may be used as a port for performing the MMS notification.

The transmission control protocol (TCP)/user datagram protocol (UDP) port may be divided into a well-known port (0 to 1023), a registered port (1024 to 49151), and a dynamic port (49152 to 65535), and a dynamic port area may be used during an execution process of the various embodiments of the present disclosure.

Figure 12A:
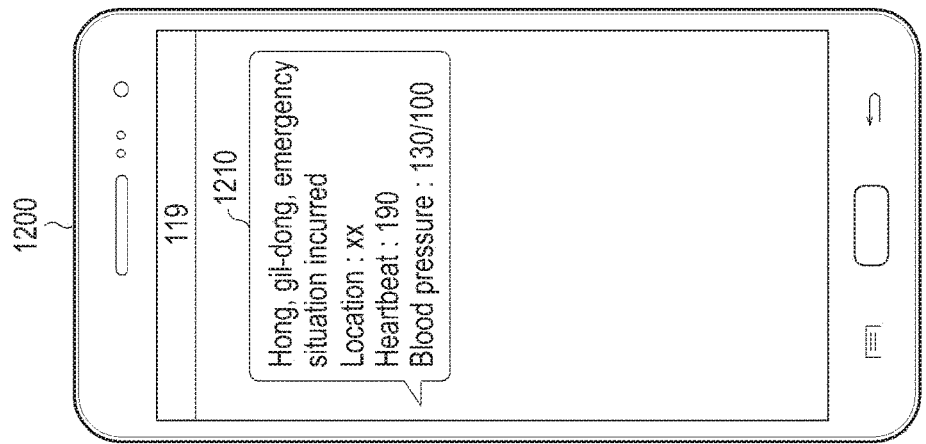
FIGS. 12A to 12C are diagrams for describing an embodiment of the present disclosure, in which health information about a help requester is transmitted through an SMS according to a request of a rescuer in an emergency mode according to various embodiments of the present disclosure.
Figure 12B:
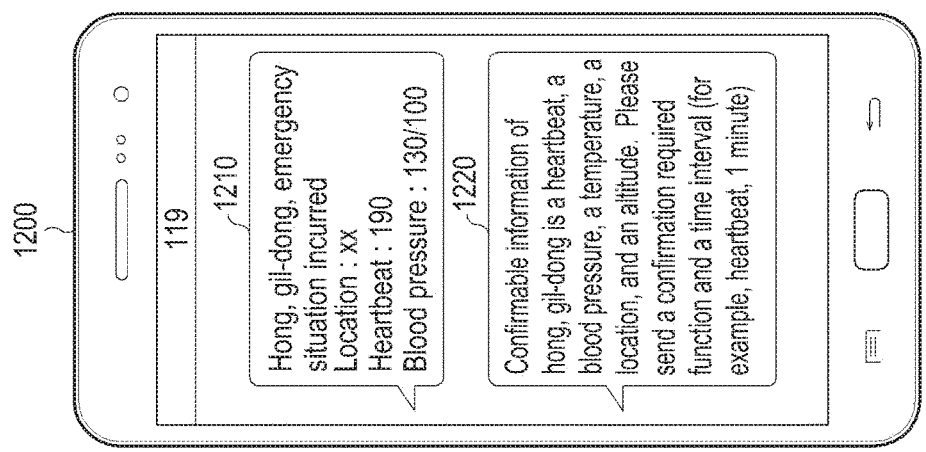
Figure 12C:
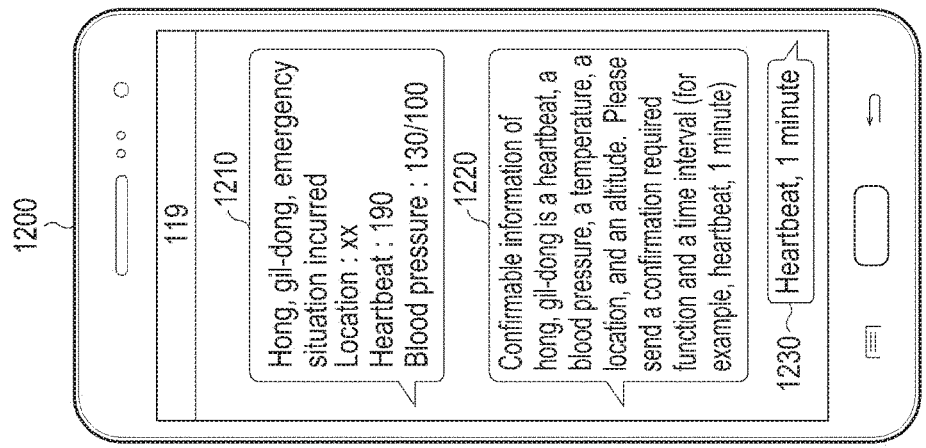

FIGS. 12A to 12C are diagrams for describing an embodiment of the present disclosure, in which health information about a help requester is transmitted through an SMS according to a request of a rescuer in an emergency mode according to various embodiments of the present disclosure.

Referring to FIG. 12A, an electronic device 1200 (for example, the electronic device 300) according to various embodiments of the present disclosure may monitor (that is, obtain) health information about the help requester according to a predetermined time interval. When the health information about the help requester passes a predetermined threshold value (for example, a heartbeat rate of 190 times), the electronic device 1200 may provide a message (for example, an emergency message 1210) including the health information about the help requester to a predesignated external device as illustrated in FIG. 12A. The health information about the help requester may also be detected by, for example, the sensor module 250, or by a wearable device worn on the help requester. The external device, to which the health information is transmitted, may include the first external electronic device or the second external electronic device.

Referring to FIG. 12B, the electronic device 1200 may provide a guidance message 1220 for the type (that is, the health capability) of health information obtainable by the electronic device 1200 or the wearable device connected with the electronic device 1200 through wireless communication to the external device (for example, the external electronic device 320). According to various embodiments of the present disclosure, the guidance message 1220 may be transmitted to the external device through the SMS.

Referring to FIG. 12C, the electronic device 1200 may transmit the health information about the help requester corresponding to a health information request message 1230 to the external device according to the health information request message 1230 received from the external device. According to various embodiments of the present disclosure, the health information request message 1230 may be transmitted through the SMS as illustrated in FIG. 12C. The electronic device 1200 may determine the contents of the health information request message 1230, and transmit the health information about the help requester to the external device based on the determined contents. Here, the health information about the help requester may contain, for example, information stored in the electronic device 1200 or information obtained (that is, has been obtained or to be obtained) by the electronic device 1200. In relation to the transmission of the health information request message 1230, the description with reference to FIGS. 11A to 11C will be referred. The electronic device 1200 may determine a message received through the specific application port described with reference to FIGS. 11A to 11C as the health information request message 1230, and may determine (that is, analyze or confirm) the contents of the health information request message 1230. According to various embodiments of the present disclosure, the port, which receives the health information request message 1230, may be the same port as the port, through which the emergency message 1210 is transmitted to the external device. The function(s) or the operation(s) described with reference to FIGS. 12A to 12C may be controlled by a processor of the electronic device 1200.

According to various embodiments of the present disclosure, the processor of the electronic device 1200 may control the SMS including the location information and the health information to be transmitted to the external device through the predesignated port.

According to various embodiments of the present disclosure, when the processor of the electronic device 1200 receives a response received from the external device through the port, through which the SMS is transmitted, the processor of the electronic device 1200 may control only the health information corresponding to the response to be provided to the external device based on the contents of the received response.

Figure 13A:
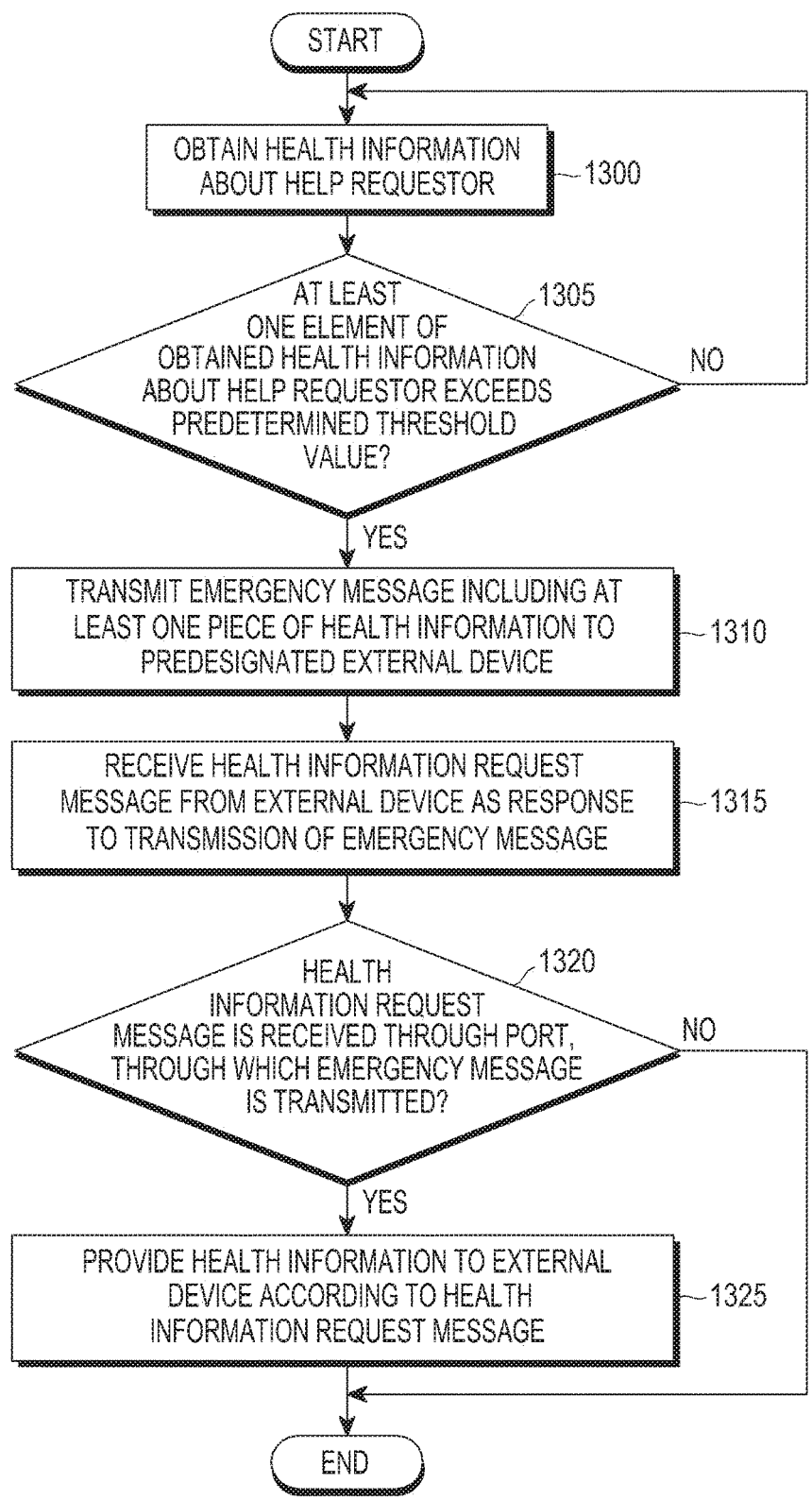
FIGS. 13A and 13B are diagrams for describing the embodiment illustrated in FIGS. 12A to 12C in more detail according to various embodiments of the present disclosure.
Figure 13B:
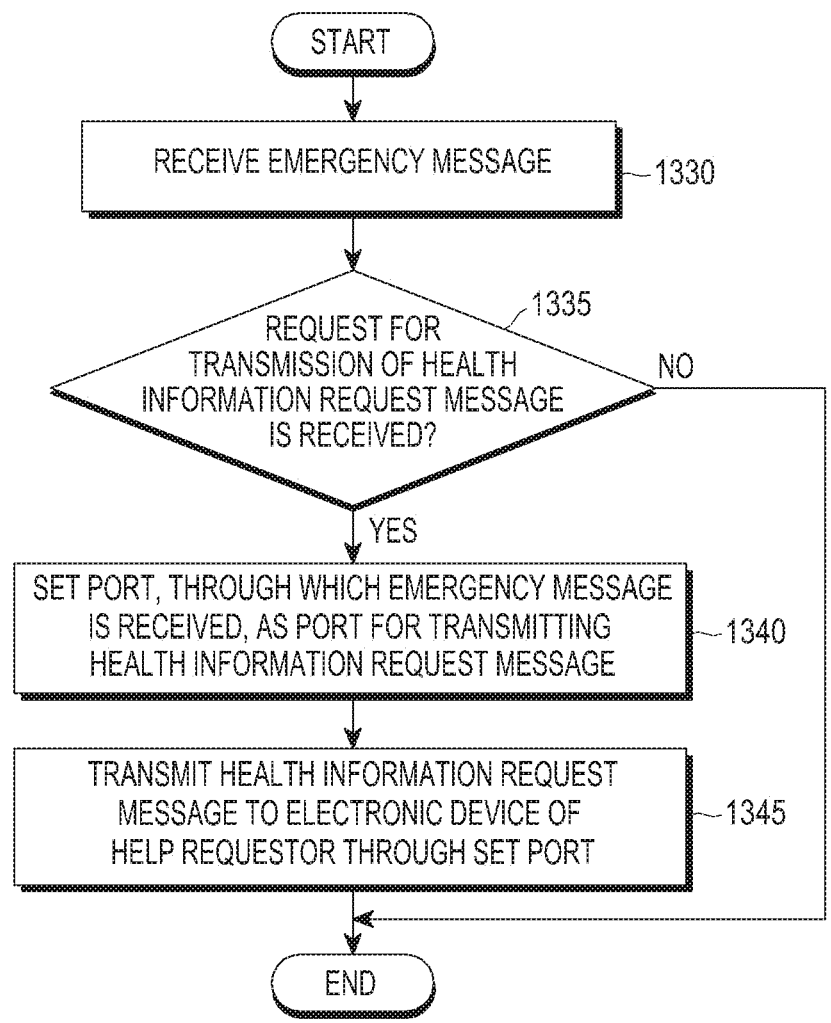

FIGS. 13A and 13B are diagrams for describing the embodiment illustrated in FIGS. 12A to 12C in more detail.

Referring to FIG. 13A, a method of operating the electronic device according to various embodiments of the present disclosure may include an operation 1300 of obtaining, by an electronic device (for example, the electronic device 300), health information about the help requester. The health information about the help requester may also be obtained by, for example, the sensor module 250, and by a method of receiving the health information obtained by a sub electronic device (for example, a wearable device) connected with the electronic device 300 through wireless communication.

The method of operating the electronic device according to various embodiments of the present disclosure may include an operation 1305 of determining whether at least one element of the obtained health information about the help requester passes a predetermined threshold value. The health information about the help requester may contain at least one of, for example, a heartbeat rate of the help requester, a blood pressure of the help requester, a temperature of the help requester, and a blood sugar level of the help requester.

The method of operating the electronic device 300 according to various embodiments of the present disclosure may include an operation 1310 of when at least one element of the obtained health information about the help requester passes the predetermined threshold value, transmitting an emergency message including at least one element of the obtained health information about the help requester to a predesignated rescuer (for example, the external electronic device 320). The operation 1310 may be performed in the emergency mode according to various embodiments of the present disclosure. That is, when at least one element of the obtained health information about the help requester passes the predetermined threshold value, the method may further include an operation of changing the operation mode of the electronic device 300 to the emergency mode. The operation of transmitting the emergency message may include, for example, transmitting a text message SMS including the health information to a telephone number (for example, 119) designated by a user (for example, the help requester) of the electronic device 300 as illustrated in FIG. 12A. According to various embodiments of the present disclosure, the predesignated telephone number may be predetermined during a manufacturing process of the electronic device 300 or may also be designated by the help requester. According to various embodiments of the present disclosure, the emergency message may include, for example, types of the health information obtainable by the electronic device 300 and/or the sub electronic device connected with the electronic device 300 through wireless communication as illustrated in FIG. 12B. The term "types of the health information obtainable by the electronic device 300 and/or the sub electronic device connected with the electronic device 300 through wireless communication" may sometimes be replaced with and used as the term "capability". FIG. 12B illustrates a heartbeat rate of the help requester, a blood pressure of the help requester, and a temperature of the help requester. According to various embodiments of the present disclosure, the emergency message may include current location information about the electronic device 300 and/or altitude information of a place at which the electronic device 300 is located. The altitude information may be sometimes referred to as a concept including the location information. The location information and/or the altitude information may be obtained by, for example, the GPS module 240.

The method of operating the electronic device 300 according to various embodiments of the present disclosure may include an operation 1315 of receiving health information request message from the help requester in response to the transmission of the emergency message. The health information request message may include information on at least one type among the types of the health information obtainable by the electronic device 300 and/or the sub electronic device connected with the electronic device 300 through wireless communication and/or an obtainment period of the health information as illustrated in FIG. 12C.

The health information request message may be received through the same port as the port, through which the emergency message is transmitted. The electronic device 300 may determine the contents (for example, text of the text message) included in the health information request message by determining the message received through the port as the health information request message. To this end, the method of operating the electronic device 300 According to various embodiments of the present disclosure may include an operation 1320 of determining whether the health information request message is received through the port, through which the emergency message is transmitted.

The method of operating the electronic device 300 according to various embodiments of the present disclosure may include an operation 1325 of when the health information request message is received through the port, through which the emergency message is transmitted as a result of the determination in operation 1320, determining the message received through the port, through which the emergency message is transmitted, as the health information request message, determining the contents (for example, text of the text message) included in the health information request message, and providing the additional information to the rescuer. However, when the message (for example, the text message) is not received, or when the message is received, but is not received through the port, through which the emergency message is transmitted, the electronic device 300 may not determine the received message as the health information request message.

In addition, the description about the electronic device 300 may be equally applied to the method of operating the electronic device 300 according to various embodiments of the present disclosure.

FIG. 13B is a diagram for describing a method of operating an external electronic device (for example, the external electronic device 320) according to various embodiments of the present disclosure.

Referring to FIG. 13B, the method of operating the external electronic device 320 according to various embodiments of the present disclosure may include an operation 1330 of receiving an emergency message from the help requester. The emergency message may include the aforementioned text message.

The method of operating the external electronic device 320 according to various embodiments of the present disclosure may include an operation 1335 of determining whether the request for the transmission of the health information request message from the electronic device 300 is received from the help requester.

The method of operating the external electronic device 320 according to various embodiments of the present disclosure may include an operation 1340 of when the request for the transmission of the health information request message from the electronic device 300 is received from the help requester, setting, by the external electronic device 320, a port, through which the emergency message, as a port for transmitting the health information request message.

The method of operating the external electronic device 320 according to various embodiments of the present disclosure may include an operation 1345 of transmitting the health information request message to the electronic device 300 through the set port.

In addition, the description related to the electronic device 300 and/or the external electronic device 320 may be equally applied to the method of operating the external electronic device 320 according to various embodiments of the present disclosure.

According to various embodiments of the present disclosure, when the help requester sends the emergency call through the electronic device 300, the emergency call may not be connected due to an unexpected situation. In this case, the processor 200 of the electronic device 300 may send the emergency message to an external electronic device (for example, the second external electronic device) having a next priority according to the predetermined priority. The priority may be predetermined by the help requester. The priority may be determined as, for example, the first priority is an emergency rescue organization, the second priority is parents of the help requester, and the third priority is predesignated acquaintances of the help requester.

According to various embodiments of the present disclosure, even if the help requester does not require the emergency rescue (that is, a physical problem is not particularly generated to the help requester), the electronic device 300 may transmit the health information about the help requester to another external electronic device (for example, the second external electronic device) according to the request of the help requester. For example, when the health information transmission request of the help requester is received during a call with an acquaintance of the help requester, the processor 200 of the electronic device 300 may control the health information about the help requester stored in the electronic device 300 to be transmitted to a counterpart (that is, the first external electronic device or the second external electronic device) of the call with the help requester. The health information may be transmitted to the counterpart of the call with the help requester through the SMS teleservice 65002 in a case of, for example, a voice call (circuit call), and may be transmitted to the counterpart of the call with the help requester through the LHP in a case of a video call (VoIP).

According to various embodiments of the present disclosure, the processor 200 of the electronic device 300 may control a notification message predesignated by the help requester to the external electronic device 320 when the call is connected with the external electronic device 320. For example, the processor 200 of the electronic device 300 may enable the rescuer to rapidly determine a body state of the help requester by transmitting a guidance message "I have diabetes" to the external electronic device 320 within a predetermined time after the call connection. Otherwise, the processor 200 of the electronic device 300 may control information (for example, current administration information related to the diabetes, and a history of visits to a hospital related to the diabetes) pre-stored in the electronic device 300 by the help requester in relation to a keyword (for example, "diabetes") predesignated by the help requester to be transmitted to the external electronic device 320 within a predetermined time after the call connection with the rescuer. However, according to various embodiments of the present disclosure, the health information about the help requester may be set not to be transmitted to the rescuer according to a request of the help requester.

According to various embodiments of the present disclosure, the electronic device 300 may obtain surrounding environment information of the electronic device 300, for example, an external temperature around the electronic device 300, altitude information about a place, at which the electronic device 300 is located, and humidity information around the electronic device 300, in addition to the location information and the health information, and provide the obtained information to the external electronic device 320. The surrounding environment information may be obtained from, for example, the sensor module 250 or the wearable device connected with the electronic device 300 through wireless communication.

According to various embodiments of the present disclosure, the electronic device 300 may control the location information and/or the health information to be periodically transmitted to the external electronic device 320 according to a uniform time interval according to a request of the external electronic device 320.

According to various embodiments of the present disclosure, the electronic device 300 may provide information (for example, a name, a telephone number, and a job of the acquaintance, and a relation of the acquaintance with the help requester) about an acquaintance (for example, a family member of the help requester and a family doctor of the help requester) predesignated by the help requester to the external electronic device 320, in addition to the location information and the health information. The acquaintance information may be provided to the external electronic device 320 as a message based on a different protocol, for example, the SMS or the TPC/IP, different from the protocol for providing the health information according to various embodiments of the present disclosure described with reference to FIGS. 4A to 10. In the present disclosure, the terms "surrounding environment information" and "acquaintance information" may be collectively referred to as the term "additional information" as necessary.

Figure 14A:
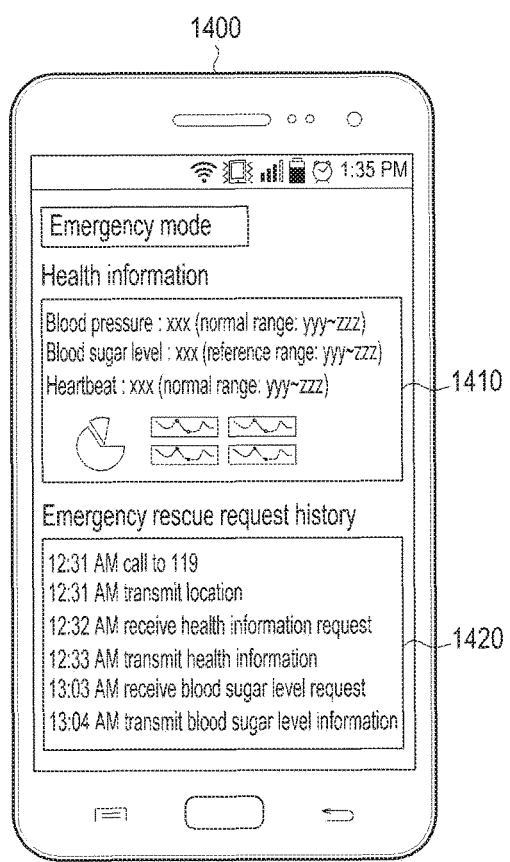
FIGS. 14A and 14B are diagrams for describing various embodiment of the present disclosure, in which health information about a help requester transmitted to an electronic device is displayed on an external electronic device according to various embodiments of the present disclosure.
Figure 14B:
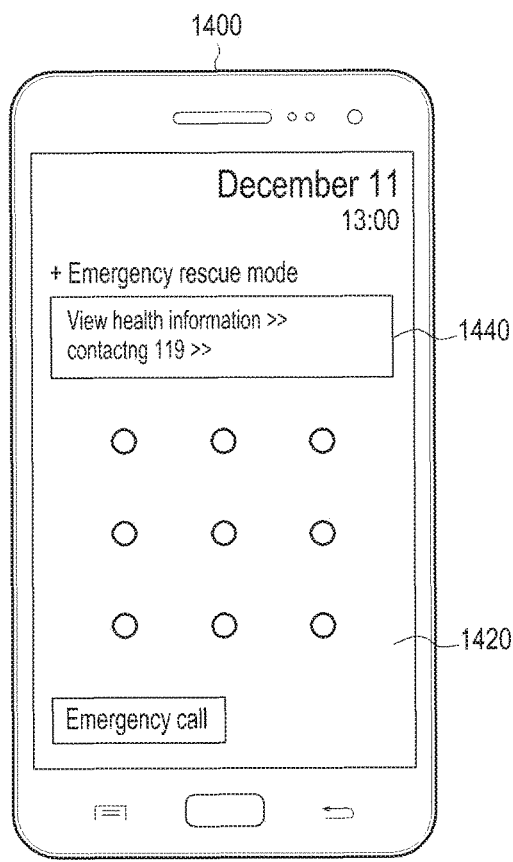

FIGS. 14A and 14B are diagrams for describing various embodiment of the present disclosure, in which health information about a help requester transmitted to an electronic device is displayed on an external electronic device according to various embodiments of the present disclosure.

Referring to FIG. 14A, when an external electronic device 1400 (for example, the external electronic device 320) is, for example, a portable terminal, health information 1410 provided from the electronic device 300 and/or help request history information 1420 about the help requester may be displayed on a home screen of the external electronic device 1400. Otherwise, as illustrated in FIG. 14B, a menu 1440 for confirming the health information and/or the help request history information may be displayed on a lock screen 1430 of the external electronic device 1400.

According to various embodiments of the present disclosure, the help requester may be a user (which may be referred to as a "help needer" for the convenience of description in the present disclosure) to which a physical problem is actually generated, but may be an eyewitness witnessing the user to which a physical problem is actually generated. When the eyewitness sends an emergency call to the emergency rescue organization, the external electronic device 320 may transmit a unique ID for an emergency rescue to the eyewitness, and the eyewitness may broadcast the received unique ID by using short range communication, such as BT. The health information about the help needer may be received from a portable terminal of the help needer receiving the unique ID through the broadcasting of the unique ID, and may be transmitted to the external electronic device 320. The unique ID may mean identification information required for an authentication for transceiving the health information.

Figure 15:
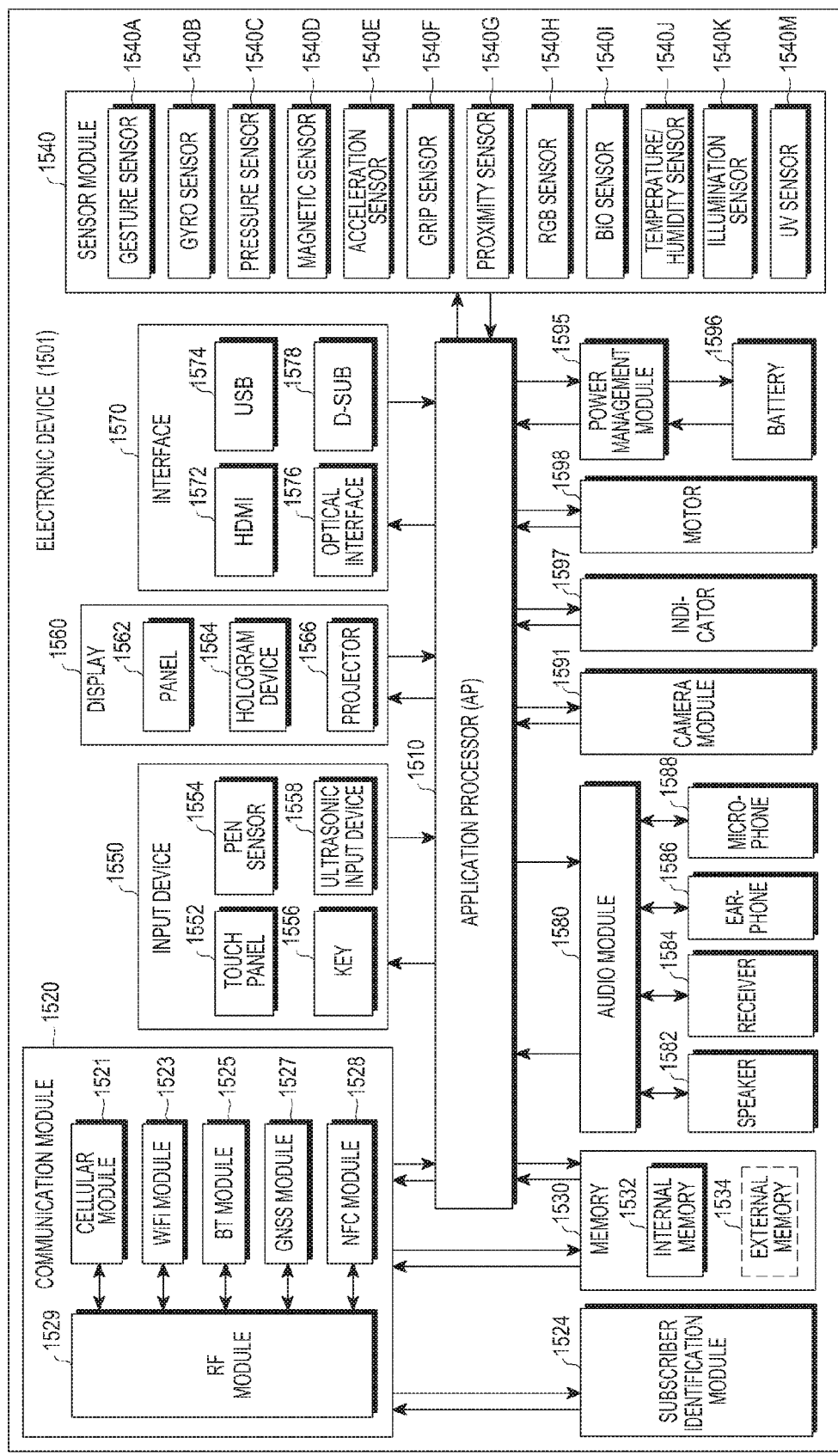
FIG. 15 is a block diagram illustrating an example of an electronic device according to various embodiments of the present disclosure.

FIG. 15 is a block diagram illustrating an example of an electronic device according to various embodiments of the present disclosure.

Referring to FIG. 15, an electronic device 1501 may include the whole or a part of the electronic device 1501 illustrated in FIG. 1A. The electronic device 1501 may include at least one AP 1510, a communication module 1520, a subscriber identification module (SIM) 1524, a memory 1530, a sensor module 1540, an input device 1550, a display 1560, an interface 1570, an audio module 1580, a camera module 1591, a power management module 1595, a battery 1596, an indicator 15915, and a motor 1598.

The processor 1510 may control a plurality of hardware or software components connected to the processor 1510 by driving an OS or an application program and perform various data processing and calculations. The processor 1510 may be implemented by, for example, a system on chip (SoC). According to an embodiment of the present disclosure, the processor 1510 may further include a graphic processing unit (GPU) and/or an image signal processor (ISP). The processor 1510 may also include at least some (for example, a cellular module 1521) of the elements illustrated in FIG. 15. The processor 1510 may load, into a volatile memory, instructions or data received from at least one (for example, a non-volatile memory) of the other elements and may process the loaded instructions or data, and may store various data in a non-volatile memory.

The communication module 1520 may have a configuration equal or similar to that of the communication interface 1150 of FIG. 1A. The communication module 1520 may include, for example, the cellular module 521, a Wi-Fi module 1523, a BT module 1525, a GNSS module 1527 (for example, a GPS module, a Glonass module, a Beidou module, or a Galileo module), an NFC module 1528, and a radio frequency (RF) module 1529.

The cellular module 1521 may provide a voice call, an image call, a text message service, or an Internet service through, for example, a communication network. According to an embodiment of the present disclosure, the cellular module 1521 may identify and authenticate the electronic device 1501 within a communication network by using the subscriber identification module 1524 (for example, an SIM card). According to an embodiment of the present disclosure, the cellular module 1521 may perform at least some of the functions that the processor 1510 may provide. According to an embodiment of the present disclosure, the cellular module 1521 may include a CP.

Each of the Wi-Fi module 1523, the BT module 1525, the GNSS module 1527, or the NFC module 1528 may include, for example, a processor that processes data transmitted and received through the corresponding module. According to some embodiments of the present disclosure, at least some (for example, two or more) of the cellular module 1521, the Wi-Fi module 1523, the BT module 1525, the GNSS module 1527, and the NFC module 1528 may be included in one integrated chip (IC) or IC package.

The RF module 1529 may transmit/receive, for example, a communication signal (for example, an RF signal). The RF module 1529 may include, for example, a transceiver, a power amp module (PAM), a frequency filter, a low noise amplifier (LNA), or an antenna. According to another embodiment of the present disclosure, at least one of the cellular module 1521, the Wi-Fi module 1523, the BT module 1525, the GNSS module 1527, and the NFC module 1528 may transmit and receive RF signals through a separate RF module.

The subscriber identification module 1524 may include, for example, a card including a subscriber identity module and/or an embedded SIM, and may contain unique identification information (for example, an integrated circuit card identifier (ICCID)) or subscriber information (for example, an international mobile subscriber identity (IMSI)).

The memory 1530 (for example, the memory 130) may include, for example, an internal memory 1532 or an external memory 1534. The internal memory 1532 may include at least one of a volatile memory (for example, a dynamic RAM (DRAM), a static RAM (SRAM), a synchronous DRAM (SDRAM), and the like) and a non-volatile memory (for example, a one time programmable ROM (OTPROM), a PROM, an erasable and programmable ROM (EPROM), an electrically erasable and programmable ROM (EEPROM), a mask ROM, a flash ROM, a flash memory (for example, a NAND flash memory or a NOR flash memory), a hard disk drive, a solid state drive (SSD), and the like).

The external memory 1534 may further include a flash drive, for example, a compact flash (CF), a secure digital (SD), a micro SD (Micro-SD), a mini SD (Mini-SD), an extreme Digital (xD), a multi-media card (MMC), a memory stick, or the like. The external memory 1534 may be functionally and/or physically connected to the electronic device 1501 through various interfaces.

The sensor module 1540 may measure a physical quantity or detect an operation state of the electronic device 1501, and may convert the measured or detected information into an electrical signal. The sensor module 1540 may include, for example, at least one of a gesture sensor 1540A, a gyro sensor 1540B, an atmospheric pressure sensor 1540C, a magnetic sensor 1540D, an acceleration sensor 1540E, a grip sensor 1540F, a proximity sensor 1540G, a color sensor 1540H (e.g., a red, green, blue (RGB) sensor), a biometric sensor 1540I, a temperature/humidity sensor 1540J, an illuminance (illumination) sensor 1540K, and a UV sensor 1540M. Additionally or alternatively, the sensor module 1540 may include, for example, an E-nose sensor, an EMG sensor, an EEG sensor, an ECG sensor, an IR sensor, an iris sensor, and/or a fingerprint sensor. The sensor module 1540 may further include a control circuit for controlling one or more sensors included therein. In some embodiments of the present disclosure, the electronic device 1501 may further include a processor configured to control the sensor module 1540 as a part of or separately from the processor 1510, and may control the sensor module 1540 while the processor 1510 is in a sleep state.

The input device 1550 may include, for example, a touch panel 1552, a (digital) pen sensor 1554, a key 1556, and an ultrasonic input unit 1558. The touch panel 1552 may use at least one of, for example, a capacitive type, a resistive type, an IR type, and an ultrasonic type. Also, the touch panel 1552 may further include a control circuit. The touch panel 1552 may further include a tactile layer and provide a tactile reaction to the user.

The (digital) pen sensor 1554 may include, for example, a recognition sheet which is a part of the touch panel or is separated from the touch panel. The key 1556 may include, for example, a physical button, an optical key, or a keypad. The ultrasonic input device 1558 may detect ultrasonic waves generated by an input tool through a microphone (for example, a microphone 1588) and identify data corresponding to the detected ultrasonic waves.

The display 1560 (for example, the display 160) may include a panel 1562, a hologram device 1564, or a projector 1566. The panel 1562 may include a configuration identical or similar to that of the display 160 illustrated in FIG. 1A. The panel 1562 may be implemented to be, for example, flexible, transparent, or wearable. The panel 1562 and the touch panel 1552 may be implemented as one module. The hologram 1564 may show a three dimensional image in the air by using an interference of light. The projector 1566 may display an image by projecting light onto a screen. The screen may be located, for example, inside or outside the electronic device 1501. According to an embodiment of the present disclosure, the display 1560 may further include a control circuit for controlling the panel 1562, the hologram device 1564, or the projector 1566.

The interface 1570 may include, for example, an HDMI 1572, a USB 1574, an optical interface 1576, or a D-sub-miniature (D-sub) 1578. The interface 1570 may be included in, for example, the communication interface 1150 illustrated in FIG. 1A. Additionally or alternatively, the interface 1570 may include, for example, a mobile high-definition link (MHL) interface, a SD card/MMC interface, or an IrDA standard interface.

The audio module 1580 may bilaterally convert, for example, a sound and an electrical signal. At least some elements of the audio module 1580 may be included in, for example, the input/output interface 145 illustrated in FIG. 1A. The audio module 1580 may process sound information which is input or output through, for example, a speaker 1582, a receiver 1584, earphones 1586, the microphone 1588 or the like.

The camera module 1591 is a device which may photograph a still image and a dynamic image. According to an embodiment of the present disclosure, the camera module 291 may include one or more image sensors (for example, a front sensor or a back sensor), a lens, an image signal processor (ISP) or a flash (for example, LED or xenon lamp).

The power management module 1595 may manage, for example, power of the electronic device 1501. According to an embodiment of the present disclosure, the power management module 1595 may include a power management integrated circuit (PMIC), a charger integrated circuit (IC), or a battery or fuel gauge. The PMIC may have a wired and/or wireless charging scheme. Examples of the wireless charging method may include, for example, a magnetic resonance method, a magnetic induction method, an electromagnetic method, and the like. Additional circuits (e.g., a coil loop, a resonance circuit, a rectifier, etc.) for wireless charging may be further included. The battery gauge may measure, for example, a residual quantity of the battery 1596, and a voltage, a current, or a temperature during the charging. The battery 1596 may include, for example, a rechargeable battery or a solar battery.

The indicator 1597 may display a particular state (for example, a booting state, a message state, a charging state, or the like) of the electronic device 1501 or a part (for example, the processor 1510) of the electronic device 1501. The motor 1598 may convert an electrical signal into mechanical vibration, and may generate vibration, a haptic effect, or the like. Although not illustrated, the electronic device 1501 may include a processing unit (for example, a GPU) for supporting a mobile television. The processing unit for supporting mobile TV may, for example, process media data according to a certain standard such as DMB, DVB, or mediaFlo™.

Each of the above-described component elements of hardware according to the present disclosure may be configured with one or more components, and the names of the corresponding component elements may vary based on the type of electronic device. The electronic device according to various embodiments of the present disclosure may include at least one of the aforementioned elements. Some elements may be omitted or other additional elements may be further included in the electronic device. Also, some of the hardware components according to various embodiments may be combined into one entity, which may perform functions identical to those of the relevant components before the combination.

Figure 16:
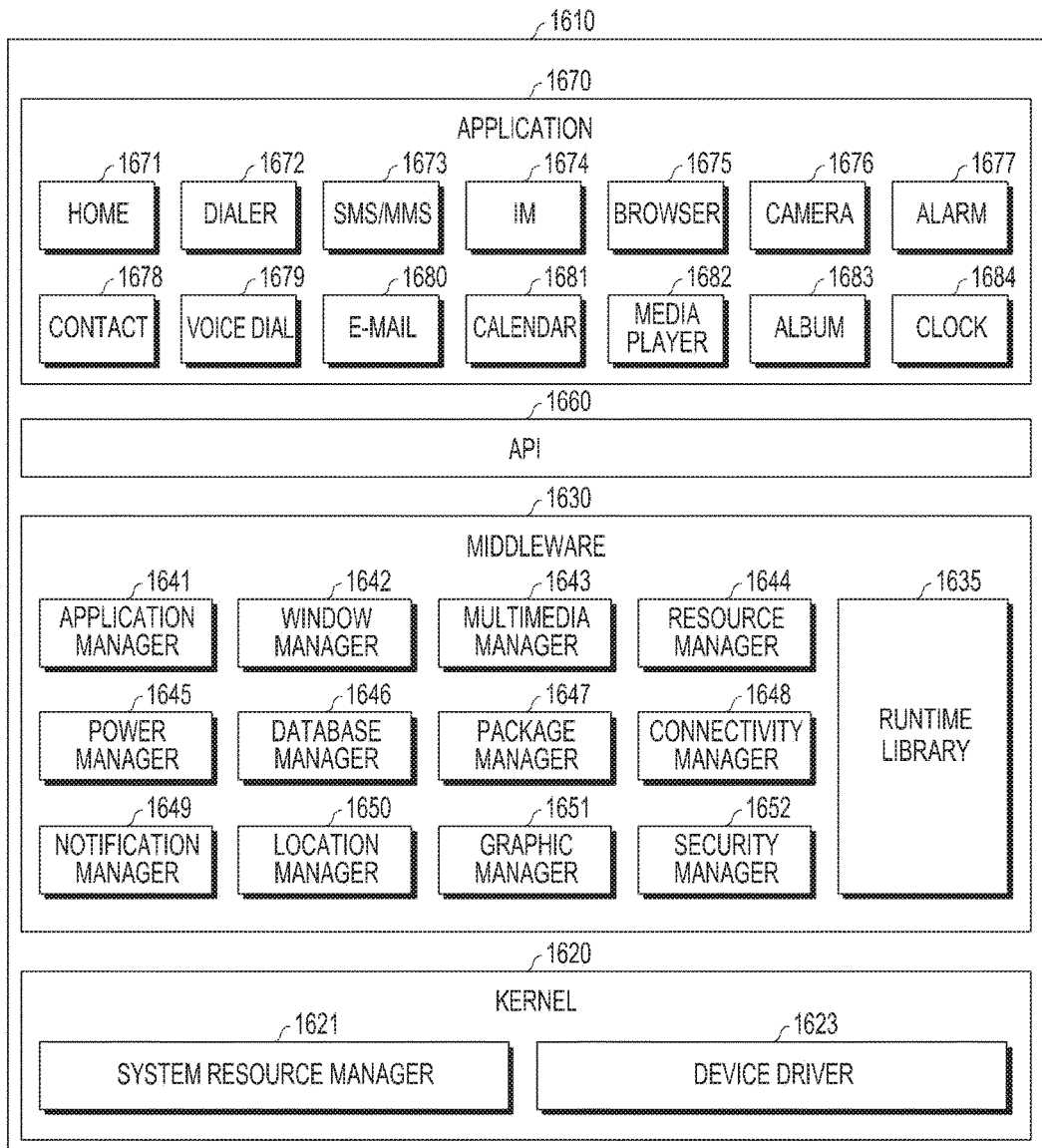
FIG. 16 is a block diagram illustrating an example of a program module according to various embodiments of the present disclosure.

FIG. 16 is a block diagram illustrating an example of a program module according to various embodiments of the present disclosure.

Referring to FIG. 16, the program module 1610 (for example, the program 140) may include an OS for controlling resources related to the electronic device (for example, the electronic device 101) and/or various applications (for example, the application programs 147) executed in the OS. The OS may be, for example, Android, iOS, Windows, Symbian, Tizen, Bada, or the like.

The program module 1610 may include a kernel 1620, middleware 1630, an API 1660, and/or applications 1670. At least some of the program module 1610 may be preloaded on the electronic device, or may be downloaded from an external electronic device (for example, the electronic device 102 or 104, or the server 106).

The kernel 1620 (for example, the kernel 141) may include, for example, a system resource manager 1621 and/or a device driver 1623. The system resource manager 1621 may perform the control, allocation, retrieval, or the like of system resources. According to an embodiment of the present disclosure, the system resource manager 1621 may include a process manager, a memory manager, a file system manager, or the like. The device driver 1623 may include, for example, a display driver, a camera driver, a BT driver, a shared memory driver, a USB driver, a keypad driver, a Wi-Fi driver, an audio driver, or an inter-process communication (IPC) driver.

The middleware 1630 may provide a function required by the applications 1670 in common or provide various functions to the applications 1670 through the API 1660 so that the applications 1670 may efficiently use limited system resources within the electronic device. According to an embodiment of the present disclosure, the middleware 1630 (for example, the middleware 143) may include, for example, at least one of a runtime library 1635, an application manager 1641, a window manager 1642, a multimedia manager 1643, a resource manager 1644, a power manager 1645, a database manager 1646, a package manager 1647, a connectivity manager 1648, a notification manager 1649, a location manager 1650, a graphic manager 1651, and a security manager 1652.

The runtime library 1635 may include a library module which a compiler uses in order to add a new function through a programming language while the applications 1670 are being executed. The runtime library 1635 may perform input/output management, memory management, the functionality for an arithmetic function, or the like.

The application manager 1641 may manage, for example, a life cycle of at least one of the applications 1670. The window manager 1642 may manage graphical user interface (GUI) resources used for the screen. The multimedia manager 1643 may determine a format required to reproduce various media files, and may encode or decode a media file by using a coder/decoder (codec) appropriate for the corresponding format. The resource manager 1644 may manage resources, such as a source code, a memory, a storage space, and the like of at least one of the applications 1670.

For example, the power manager 1645 may operate together with a basic input/output system (BIOS), etc. and may manage a battery or power, and may provide power information and the like required for an operation of the electronic apparatus. The database manager 1646 may generate, search for, and/or change a database to be used by at least one of the applications 1670. The package manager 1647 may manage the installation or update of an application distributed in the form of a package file.

The connectivity manager 1648 may manage a wireless connection such as, for example, Wi-Fi or BT. The notification manager 1649 may display or notify of an event, such as an arrival message, an appointment, a proximity notification, and the like, in such a manner as not to disturb the user. The location manager 1650 may manage location information of the electronic device. The graphic manager 1651 may manage a graphic effect, which is to be provided to the user, or a UI related to the graphic effect. The security manager 1652 may provide various security functions required for system security, user authentication, and the like. According to an embodiment of the present disclosure, when the electronic device (for example, the electronic device 101) has a telephone call function, the middleware 1630 may further include a telephony manager for managing a voice call function or a video call function of the electronic device.

The middleware 1630 may include a middleware module that forms a combination of various functions of the above-described elements. The middleware 1630 may provide a module specialized for each type of OS in order to provide a differentiated function. Also, the middleware 1630 may dynamically delete some of the existing elements, or may add new elements.

The API 1660 (e.g., the API 145) may be, for example, a set of API programming functions and may have different configurations according to OSs. For example, in the case of Android or iOS, one API set may be provided for each platform. In the case of Tizen, two or more API sets may be provided for each platform.

The applications 1670 (for example, the application programs 147) may include, for example, one or more applications which can provide functions such as home 1671, dialer 1672, SMS/MMS 1673, instant message (IM) 1674, browser 1675, camera 1676, alarm 1677, contacts 1678, voice dialer 1679, email 1680, calendar 1681, media player 1682, album 1683, clock 1684, health care (for example, measure exercise quantity or blood sugar), or environment information (for example, atmospheric pressure, humidity, or temperature information).

According to an embodiment of the present disclosure, the applications 1670 may include an application (hereinafter, referred to as an "information exchange application" for convenience of description) supporting information exchange between the electronic device (for example, the electronic device 101) and an external electronic device (for example, the electronic device 102 or 104). The information exchange application may include, for example, a notification relay application for transferring specific information to an external electronic device or a device management application for managing an external electronic device.

For example, the notification relay application may include a function of transferring, to the external electronic device (for example, the electronic device 102 or 104), notification information generated from other applications of the electronic device (for example, an SMS/MMS application, an e-mail application, a health management application, or an environmental information application). Further, the notification relay application can, for example, receive notification information from the external electronic device and provide the received notification information to a user.

The device management application may manage (for example, install, delete, or update), for example, at least one function of an external electronic device (for example, the electronic device 102 or 104) communicating with the electronic device (for example, a function of turning on/off the external electronic device itself (or some components) or a function of adjusting luminance (or a resolution) of the display), applications operating in the external electronic device, or services provided by the external electronic device (for example, a call service and a message service).

According to an embodiment of the present disclosure, the applications 1670 may include applications (for example, a health care application of a mobile medical appliance or the like) designated according to attributes of the external electronic device 102 or 104. According to an embodiment of the present disclosure, the application 1670 may include an application received from the external electronic device (for example, the server 106, or the electronic device 102 or 104). According to an embodiment of the present disclosure, the application 1670 may include a preloaded application or a third party application which can be downloaded from the server. Names of the elements of the program module 1610, according to the above-described embodiments of the present disclosure, may change depending on the type of OS.

According to various embodiments of the present disclosure, at least some of the program module 1610 may be implemented in software, firmware, hardware, or a combination of two or more thereof. At least some of the program module 1610 may be implemented (e.g., executed) by, for example, the processor (e.g., the processor 210). At least some of the program module 1610 may include, for example, a module, a program, a routine, a set of instructions, and/or a process for performing one or more functions.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to the present disclosure may include at least one of an application-specific integrated circuit (ASIC) chip, a field-programmable gate arrays (FPGA), and a programmable-logic device for performing operations which has been known or are to be developed hereinafter.

According to various embodiments of the present disclosure, at least some of the devices (for example, modules or functions thereof) or the method (for example, operations) according to the present disclosure may be implemented by a command stored in a computer-readable storage medium in a programming module form. The instruction, when executed by a processor (e.g., the processor 120), may cause the one or more processors to execute the function corresponding to the instruction. The computer-readable storage medium may be, for example, the memory 130.

The computer readable recoding medium may include a hard disk, a floppy disk, magnetic media (e.g., a magnetic tape), optical media (e.g., a compact disc ROM (CD-ROM) and a DVD), magneto-optical media (e.g., a floptical disk), a hardware device (e.g., a ROM, a RAM, a flash memory), and the like. In addition, the program instructions may include high class language codes, which can be executed in a computer by using an interpreter, as well as machine codes made by a compiler. The aforementioned hardware device may be configured to operate as one or more software modules in order to perform the operation of the present disclosure, and vice versa.

The programming module according to the present disclosure may include one or more of the aforementioned components or may further include other additional components, or some of the aforementioned components may be omitted. Operations executed by a module, a programming module, or other component elements according to various embodiments of the present disclosure may be executed sequentially, in parallel, repeatedly, or in a heuristic manner. Further, some operations may be executed according to another order or may be omitted, or other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device comprising:
    a housing;
    a biometric sensor that is disposed within the housing and obtains health information about a user of the electronic device; and
    a processor which is disposed within the housing and is connected with the biometric sensor,
    wherein the processor is configured to:
        control to transmit a message including a type of the health information to a first external device, based on a change of the health information, wherein the type of the health information includes obtainable health information by the biometric sensor,
        control to receive a response, corresponding to the transmitted message, from the first external device, the response including a type of at least one piece of the health information from the type of the health information, and
        control to transmit health information corresponding to the received type of at least one piece of the health information to the first external device, according to the response.

2. The electronic device of claim 1, wherein the processor sets a single session for transmitting a location information and the health information to the first external electronic device.

3. The electronic device of claim 1, wherein the processor is further configured to set:
    a first session for transmitting the location information to the first external electronic device, and
    a second session for transmitting the health information to the first external electronic device.

4. The electronic device of claim 3, wherein each of the first and second sessions comprises a session for direct communication with a second external electronic device connected with the electronic device through wireless communication.

5. The electronic device of claim 1, wherein, when an emergency mode is entered, the processor is further configured to control a guidance message pre-stored in the electronic device in relation to the health information to be transmitted to the first external electronic device.

6. The electronic device of claim 1, wherein the processor is further configured to transmit additional information obtained by the electronic device to the first external electronic device together with the location information and the health information.

7. The electronic device of claim 6, wherein the additional information comprises at least one of:
    at least one element of information on an environment temperature around the electronic device,
    a name,
    a telephone number,
    a job, or
    a family relation of a predesignated second user.

8. The electronic device of claim 1, wherein, when the processor receives a unique identifier (ID) for receiving the location information and the health information from a second external electronic device, the processor is further configured to control the location information and the health information to be transmitted to the second external electronic device.

9. A method of operating an electronic device comprising:
    transmitting a message including a type of the health information to a first external device, based on a change of a health information, wherein the type of the health information includes obtainable health information by the biometric sensor;
    receiving a response corresponding to the transmitted message from the first external device, the response including a type of at least one piece of the health information from the type of the health information; and
    when a change of the operation mode to the emergency mode is determined, transmitting health information corresponding to the received type of at least one piece of the health information to the first external device.

10. The method of claim 9, further comprising:
    setting a single session for transmitting a location information and the health information to the first external electronic device.

11. The method of claim 9, further comprising:
setting a first session for transmitting a location information to the first external electronic device; and
setting a second session for transmitting the health information to the first external electronic device.

12. The method of claim 11, wherein the first session for transmitting the location information and the second session for transmitting the health information comprise sessions for direct communication with a second external electronic device connected with the electronic device through wireless communication.

13. The method of claim 9, further comprising:
when the operation mode enters the emergency mode, controlling a guidance message pre-stored in the electronic device in relation to the health information to be transmitted to the first external electronic device.

14. The method of claim 9, further comprising:
transmitting additional information obtained by the electronic device to the first external electronic device together with the location information and the health information.

15. The method of claim 14, wherein the additional information comprises at least one of:

at least one element of information on an environment temperature around the electronic device,
a name,
a telephone number,
a job, or
a family relation of a predesignated second user.

16. The method of claim 9, further comprising:
transmitting a request message requesting a display of the location information and the health information, which are transmitted to the first external electronic device, for a predetermined time to the external electronic device.

17. The method of claim 9, further comprising:
when a unique ID for receiving the location information and the health information is received from a second external electronic device, transmitting the location information and the health information to the second external electronic device.

18. The method of claim 9, further comprising:
requesting a sending of a call to a predesignated emergency number.

* * * * *